(12) United States Patent
Kull et al.

(10) Patent No.: US 8,741,307 B2
(45) Date of Patent: Jun. 3, 2014

(54) HYBRID PROKARYOTIC-EUKARYOTIC TUBULINS AND USE THEREOF

(75) Inventors: F. Jon Kull, Enfield, NH (US); Jared C. Cochran, Bloomington, IN (US)

(73) Assignee: Trustees of Dartmouth College, Hanover, NH (US)

( * ) Notice: Subject to any disclaimer, the term of this patent is extended or adjusted under 35 U.S.C. 154(b) by 249 days.

(21) Appl. No.: 13/266,582

(22) PCT Filed: Apr. 19, 2010

(86) PCT No.: PCT/US2010/031569
§ 371 (c)(1),
(2), (4) Date: Oct. 27, 2011

(87) PCT Pub. No.: WO2010/126732
PCT Pub. Date: Nov. 4, 2010

(65) Prior Publication Data
US 2012/0045785 A1 Feb. 23, 2012

Related U.S. Application Data

(60) Provisional application No. 61/173,687, filed on Apr. 29, 2009.

(51) Int. Cl.
*A61K 38/00* (2006.01)
*C12N 1/20* (2006.01)
*C12N 15/00* (2006.01)
*C07H 21/04* (2006.01)

(52) U.S. Cl.
USPC .... 424/192.1; 435/18; 435/252.3; 435/320.1; 536/23.4

(58) Field of Classification Search
CPC ..... A61K 38/00; A61K 39/00; C07K 2319/00
USPC .................. 435/18, 252.3, 320.1; 424/192.1; 536/23.4
See application file for complete search history.

(56) References Cited

U.S. PATENT DOCUMENTS

2007/0149496 A1 * 6/2007 Tuszynski et al. ............ 514/184

OTHER PUBLICATIONS

Bertrand et al. "Folding, Stability and Polymerization Properties of FtsZ Chimeras with Inserted Tubulin Loops Involved in the Interaction with the Cytosolic Chaperonin CCT and in Microtubule Formation" Journal of Molecular Biology 2005 346:319-330.
Bond et al. "A Chicken-Yeast Chimeric β-Tubulin Protein is Incorporated into Mouse Microtubules In Vivo" Cell 1986 44:461-468.
Chen, Y. and Erickson, H. P. "In Vitro Assembly Studies of FtsZ/Tubulin-like Proteins (TubZ) from *Bacillus* Plasmids" The Journal of Biological Chemistry 2008 283 (13) :8102-8109.
Cross, R. "Bionanotechnology: Interdisciplinary Research Collaboration" Molecular Motors Group 2009 http://mc11.mcri.ac.uk/motorhome.html.
Downing, K. H. and Nogales, E. "Crystallographic Structure of Tubulin: Implications for Dynamics and Drug Binding" Cell Structure and Function 1999 24:269-275.
Fridovich-Keil et al. "Domains of β-Tubulin Essential for Conserved Functions In Vivo" Molecular and Cellular Biology 1987 7(10):3792-3798.
Jenkins et al. "Genes for the Cytoskeletal Protein Tubulin in the Bacterial Genus *Prosthecobacter*" Proceedings of the National Academy of Sciences USA 2002 99(26):17049-17054.
Larsen et al. "Treadmilling of a Prokaryotic Tubulin-like Protein, TubZ, Required for Plasmid Stability in *Bacillus thuringiensis*" Genes & Development 2007 21:1340-1352.
Löwe et al. "Refined Structure of αβ-tubulin at 3.5 Å Resolution" Journal of Molecular Biology 2001 313(5):1045-1057.
Löwe, J. and Amos, L. A. "Crystal Structure of the Bacterial Cell-division Protein FtsZ" Nature 1998 391(6663):203-206.
Nogales et al. "Structure of Tubulin at 6.5 Å and Location of the Taxol-binding Site" Nature 1995 375(6530):424-427.
Pogliano, J. "The Bacterial Cytoskeleton" Current Opinion in Cell Biology 2008 20(1):19-27.
Schlieper et al. "Structure of Bacterial Tubulin BtubA/B: Evidence for Horizontal Gene Transfer" Proceedings of the National Academy of Sciences USA 2005 102 (26):9170-9175.
Sontag et al. "In Vitro Assembly and GTP Hydrolysis by Bacterial Tubulins BtubA and BtubB" The Journal of Cell Biology 2005 169(2):233-238.
UNIPROTKP/SWISS-PROT. Q8GCC5 [online] Mar. 1, 2003 [retrieved Jun. 24, 2010] Available on the internet <URL: http://www.uniprot.org/uniprot/Q8GCC5>.

* cited by examiner

*Primary Examiner* — Tekchand Saidha
(74) *Attorney, Agent, or Firm* — Licata & Tyrrell P.C.

(57) ABSTRACT

The present invention embraces hybrid *Prosthecobacter*-eukaryotic tubulin proteins and use thereof for identifying agents that modulate the activity of tubulin.

14 Claims, 2 Drawing Sheets

TUBULIN A

```
Pdej    MKVNNTIVVSIGQAGNQIAASFWKTVCLEHGIDPLTGQTAPGVAPRGNWSSFFSKLGESS
Pvan    MKVNNTIVISIGQAGNQIAASFWKTICQEHGIDPMTGQTAQGQAPRGNWSAFFTKLGEST
Pdeb    MKVNNTIVVSIGQAGNQIAASFWKTICQEHGIDPLTGQTAGGATPRGNWSAFFSSLGDSG
        ********:***********:*  ******:***** *  ******:**::**:*
Cons.   MKVNNTIVXSIGQAGNQIAASFWKTXCXEHGIDPXTGQTAXGXXPRGNWSXFFXXLGXSX Pdej    SGSYVPRAIMVDLEPSVIDNVKATSGSLFNPANLISRTEGAGGNFAVGYLGAGREVLPEV
Pvan    SGSYVPRAVMVDLEPSVIDNIKATSGSLFNPGNLISRTEGAGGNFAVGYLGAGREVLPEV
Pdeb    GGSFVPRAVMVDLEPSVINQVKSTSGSLFNPANLISRTEGAGGNFAVGYLGAGREVLPEV
        .**:****:*********:::*:*******.*****************************
Cons.   XGSXVPRAXMVDLEPSVIXXXKXTSGSLFNPXNLISRTEGAGGNFAVGYLGAGREVLPEV Pdej    MSRLDYEIDKCDNVGGIIVLHAIGGGTGSGFGALLIESLKEKYGEIPVLSCAVLPSPQVS
Pvan    MSRLDSEIDKCDNVGGIIVLHATGGGSGSGFGALLIESIKEKYPEFPVLSCAVLPSPQVS
Pdeb    MSRLDFEIDKCDNVGGIIVLHAIGGGSGSGLGCLLIESLKEKYPEYPVLSCAVLPSPQVS
        *****.***************.***.***:.*:*****:**** * **************
Cons.   MSRLDXEIDKCDNVGGIIVLHAXGGGXGSGXGXLLIESXKEKYXEXPVLSCAVLPSPQVS Pdej    SVVTEPYNTVFALNTLRRSADACLIFDNEALFDLAHRKWNIESPTVDDLNLLITEALAGI
Pvan    SVVTEPYNTVFTLNTLRRAADACLIFDNEALFELAHRKWNIESPTVDDLNLLITEALAGL
Pdeb    SVVTEPYNTVFALNTLRRAADACLIFDNEALFDLAHRKWNIESPTVDDLNLLITEALAGI
        ***********:******:************:***************************:
Cons.   SVVTEPYNTVFXLNTLRRXADACLIFDNEALFXLAHRKWNIESPTVDDLNLLITEALAGX Pdej    TASMRFSGFLTVEITLRELLTNLVPQPSLHFLMCAFAPLTPPDRSKFEELGIEEMIKSLF
Pvan    TASMRFSGFLTVEISLRELLTNLVPQPSLHFLMCSFAPLTPPDRSKFEEMGVEEMIRSLF
Pdeb    TASMRFSGFLTVEISLRELLTNLVPQPSLHFLMCAFAPLTAPDRSKFEEMGIEDMIRSLF
        **************:******************:******.*******:*:*:*:****
Cons.   TASMRFSGFLTVEIXLRELLTNLVPQPSLHFLMCXFAPLTXPDRSKFEEXGXEXMIXSLF Pdej    DNGSVFAACSPMEGRFLSTAVLYRGIMEDKPLADAALAAMREKLPLTYWIPTAFKIGYVE
Pvan    DNGSVFAACSPMEGRFLSTAVLYRGIMEDKPLADSALAAMREQLPLTYWIPTAFKIGYVE
Pdeb    DNDSVYAACSPMEGRFLSTAVLYRGIMEDKPLADAALAAMREKLPLTYWIPTAFKIGYVE
        **.**:***************************:*******:*****************
Cons.   DNXSVXAACSPMEGRFLSTAVLYRGIMEDKPLADXALAAMREXLPLTYWIPTAFKIGYVE Pdej    QPGISHRKSMVLLANNTEIARVLDRICHNFDKLWQRKAFANWYLNEGMSEEQINVLRASA
Pvan    QAGISHRKSMVLLANNTEIARVLDRICHNFDKLWQRKAFANWYLNEGMSEEQINALRASA
Pdeb    QSGISHRKSMVLLANNTEIARVLDRICHNFDKLWQRKAFANWYLNEGMSEEQINGLRASA
        *.**********************************************************
Cons.   QXGISHRKSMVLLANNTEIARVLDRICHNFDKLWQRKAFANWYLNEGMSEEQINXLRASA
                                                                SEQ
                                                                ID NO:
Pdej    QELVQSYQVAEESGAKAKVQDSAGDTGMRAAAAGVSDDARGSMSLRDLVDRRR-    1
Pvan    QELIQSYQVAEESGAKAKVQDSSADY-PRSSAS-SDDSRSGMSLRDLVDRRRA      3
Pdeb    QELIQSYQVAEESGAKAKIQDVSGETVSRSSSM---DDPRSTMSLRDLVERRR-     5
        ***:**************:**  ::.:  *:::   **.*.*******:***
Cons.   QELXQSYQVAEESGAKAKXQDXXXXXXXRXXXXXXXDDXRXXMSLRDLVXRRR      7
```

*FIG. 1A*

TUBULIN B

```
Pdej    VREILSIHVGQCGNQIADSFWRLALREHGLTEAGTLKEGSNAAANSNMEVFFHKVRDGKY
Pdeb    MREILSIHVGQCGNQIADSFWRLALKEHGLTETGTLKEGANAAANSDLEVFFHRVREGKY
Pvan    MREILSIHVGQCGNQIADRFWRLVLREHGLTEAGTPKEGTNVAANANMEVFFHKVRDGKY
        :****************.****.*:******:** ***:*.***:::*****:**:***
Cons.   XREILSIHVGQCGNQIADXFWRLXLXEHGLTEXGTXKEGXNXAANXXXEVFFHXVRXGKY Pdej    VPRAVLVDLEPGVIARIEGGDMSQLFDESSIVRKIPGAANNWARGYNVEGEKVIDQIMNV
Pdeb    VPRAVLIDLEPGVIGRIESGDMSKLFDESCIVRKIPGAANNWARGYHAEGKRVIDQIMNV
Pvan    IPRAILVDLEPGVIARIEGGDMAQLFDESCIIRKIPGAANNWARGYNVEGERIIDQIMNV
        :***:*:*******.***.***::.*****.*:**************:.**::.*******
Cons.   XPRAXLXDLEPGVIXRIEXGDMXXLFDESXIXRKIPGAANNWARGYXXEGXXXIDQIMNV Pdej    IDSAVEKTKGLQGFLMTHSIGGGSGSGLGSLILERLRQAYPKKRIFTFSVVPSPLISDSA
Pdeb    IDSAVEKTKGLQGFLLTHSIGGGSGSGLGSLILERLRQAYPKKRIFTFSVVPSPLISDSA
Pvan    IDAAVEKTKSLQGFLLTHSIGGGSGSGLGSLILERLRQAYPKKRIFTFSVAPSPLISDSA
        **:******.*****.************************************.*********
Cons.   IDXAVEKTKXLQGFLXTHSIGGGSGSGLGSLILERLRQAYPKKRIFTFSVXPSPLISDSA Pdej    VEPYNAILTLQRILDNADGAVLLDNEALFRIAKAKLNRSPNYMDLNNIIALIVSSVTASL
Pdeb    VEPYNAILTLKRLLDHADGSVLLDNEALFRIAKXKLNRSPTYMDLNNIIALIVSSVTASL
Pvan    VEPYNAILTLQRILDNADAAVLLDNEALFRIAKSKLHRSPNYMDLNHIIALIMSSVTASL
        **********:*:**:**..:**************  **:***.*****:*****:*******
Cons.   VEPYNAILTLXRXLDNADXXVLLDNEALFRIAKXKLXRSPXYMDLXNIIALXSSVTASL Pdej    RFPGKLNTDLSEFVTNLVPFPGNHFLTASFAPMRGAGQEGQVRTNFPDLARETFAQDNFT
Pdeb    RFPGKLNTDLSEFVTNLVPFPGNHFLTASFAPMRTADDESQVRMSFPELARETFAQDNFT
Pvan    RFPGKLNTDLGEYVTNLVPFPGNHFLTASFAPMRAPGQEGQVRINFPDIARETFAQDNFT
        **********.*:*********************   ..:*.***  .**::************
Cons.   RFPGKLNTDLXEXVTNLVPFPGNHFLTASFAPMRXXXXEXQVRXXFPXXARETFAQDNFT Pdej    AAIDWQQGVYLAASALFRGDVKAKDVDENMATIRKSLNYASYMPASGGLKLGYAETAPEG
Pdeb    AEIDWQNGVYLAASALFRGEVKAKEVDENMATIRKELNYASYMPASGGLKLGYAETAPAG
Pvan    AAIDWTNGVYLSACALFRGDVKAKEVEENMAAIRKSLNFASYVPT--GVKLGVAETAPEG
        * ***  :****:*.*****:*****:*:****.***:**:***:*:  *:***.***** *
Cons.   AXIDWXXGVYLXAXALFRGXVKAKXVXENMAXIRKXLNXASYXPXXGXLKLXYAETAXEX Pdej    FASSGLALVNHTGIAAVFERLIAQFDIMFDNHAYTHWYENAGVSRDMMAKARNQIATLAQ
Pdeb    FASSGLALVNHTGISAVFERLIGQFDIMFDNHAYTHWYENAGVSRDQMAVARDQIANLAL
Pvan    FASSGLALVNHTGIAAVFERLINNFDIMFDNHAYTHWYENNGVSRDMMAHARNTIVNLAQ
        *************:****** :. ****************..****** **.:**:.**
Cons.   FASSGLALVNHTGIXAVFERLIXXFDIMFDNHAYTHWYENXGVSRDXMAXARXXIXXLAX Pdej    SYRDAS  (SEQ ID NO:2)
Pdeb    SYRDAS  (SEQ ID NO:6)
Pvan    SYRDAS  (SEQ ID NO:4)
        ******
Cons.   SYRDAS  (SEQ ID NO:8)
```

FIG. 1B

SEQUENCE LISTING

<160> NUMBER OF SEQ ID NOS: 15

<210> SEQ ID NO 1
<211> LENGTH: 473
<212> TYPE: PRT
<213> ORGANISM: Prosthecobacter dejongeii

<400> SEQUENCE: 1

Met Lys Val Asn Asn Thr Ile Val Val Ser Ile Gly Gln Ala Gly Asn
1               5                   10                  15

Gln Ile Ala Ala Ser Phe Trp Lys Thr Val Cys Leu Glu His Gly Ile
            20                  25                  30

Asp Pro Leu Thr Gly Gln Thr Ala Pro Gly Val Ala Pro Arg Gly Asn
        35                  40                  45

Trp Ser Ser Phe Phe Ser Lys Leu Gly Glu Ser Ser Gly Ser Tyr
    50                  55                  60

Val Pro Arg Ala Ile Met Val Asp Leu Glu Pro Ser Val Ile Asp Asn
65                  70                  75                  80

Val Lys Ala Thr Ser Gly Ser Leu Phe Asn Pro Ala Asn Leu Ile Ser
                85                  90                  95

Arg Thr Glu Gly Ala Gly Gly Asn Phe Ala Val Gly Tyr Leu Gly Ala
            100                 105                 110

Gly Arg Glu Val Leu Pro Glu Val Met Ser Arg Leu Asp Tyr Glu Ile
        115                 120                 125

Asp Lys Cys Asp Asn Val Gly Gly Ile Ile Val Leu His Ala Ile Gly
    130                 135                 140

Gly Gly Thr Gly Ser Gly Phe Gly Ala Leu Leu Ile Glu Ser Leu Lys
145                 150                 155                 160

Glu Lys Tyr Gly Glu Ile Pro Val Leu Ser Cys Ala Val Leu Pro Ser
                165                 170                 175

Pro Gln Val Ser Ser Val Val Thr Glu Pro Tyr Asn Thr Val Phe Ala
            180                 185                 190

Leu Asn Thr Leu Arg Arg Ser Ala Asp Ala Cys Leu Ile Phe Asp Asn
        195                 200                 205

Glu Ala Leu Phe Asp Leu Ala His Arg Lys Trp Asn Ile Glu Ser Pro
    210                 215                 220

Thr Val Asp Asp Leu Asn Leu Ile Thr Glu Ala Leu Ala Gly Ile
225                 230                 235                 240

Thr Ala Ser Met Arg Phe Ser Gly Phe Leu Thr Val Glu Ile Thr Leu
                245                 250                 255

Arg Glu Leu Leu Thr Asn Leu Val Pro Gln Pro Ser Leu His Phe Leu
            260                 265                 270

Met Cys Ala Phe Ala Pro Leu Thr Pro Pro Asp Arg Ser Lys Phe Glu
        275                 280                 285

Glu Leu Gly Ile Glu Glu Met Ile Lys Ser Leu Phe Asp Asn Gly Ser
    290                 295                 300

Val Phe Ala Ala Cys Ser Pro Met Glu Gly Arg Phe Leu Ser Thr Ala
305                 310                 315                 320

Val Leu Tyr Arg Gly Ile Met Glu Asp Lys Pro Leu Ala Asp Ala Ala
                325                 330                 335

Leu Ala Ala Met Arg Glu Lys Leu Pro Leu Thr Tyr Trp Ile Pro Thr
            340                 345                 350

Ala Phe Lys Ile Gly Tyr Val Glu Gln Pro Gly Ile Ser His Arg Lys
        355                 360                 365

```
Ser Met Val Leu Leu Ala Asn Asn Thr Glu Ile Ala Arg Val Leu Asp
    370                 375                 380

Arg Ile Cys His Asn Phe Asp Lys Leu Trp Gln Arg Lys Ala Phe Ala
385                 390                 395                 400

Asn Trp Tyr Leu Asn Glu Gly Met Ser Glu Gln Ile Asn Val Leu
                405                 410                 415

Arg Ala Ser Ala Gln Glu Leu Val Gln Ser Tyr Gln Val Ala Glu Glu
                420                 425                 430

Ser Gly Ala Lys Ala Lys Val Gln Asp Ser Ala Gly Asp Thr Gly Met
            435                 440                 445

Arg Ala Ala Ala Gly Val Ser Asp Asp Ala Arg Gly Ser Met Ser
450                 455                 460

Leu Arg Asp Leu Val Asp Arg Arg
465                 470

<210> SEQ ID NO 2
<211> LENGTH: 426
<212> TYPE: PRT
<213> ORGANISM: Prosthecobacter dejongeii

<400> SEQUENCE: 2

Val Arg Glu Ile Leu Ser Ile His Val Gly Gln Cys Gly Asn Gln Ile
1               5                   10                  15

Ala Asp Ser Phe Trp Arg Leu Ala Leu Arg Glu His Gly Leu Thr Glu
                20                  25                  30

Ala Gly Thr Leu Lys Glu Gly Ser Asn Ala Ala Ala Ser Asn Met
            35                  40                  45

Glu Val Phe Phe His Lys Val Arg Asp Gly Lys Tyr Val Pro Arg Ala
50                  55                  60

Val Leu Val Asp Leu Glu Pro Gly Val Ile Arg Ile Glu Gly Gly
65                  70                  75                  80

Asp Met Ser Gln Leu Phe Asp Glu Ser Ser Ile Val Arg Lys Ile Pro
                85                  90                  95

Gly Ala Ala Asn Asn Trp Ala Arg Gly Tyr Asn Val Glu Gly Glu Lys
            100                 105                 110

Val Ile Asp Gln Ile Met Asn Val Ile Asp Ser Ala Val Glu Lys Thr
            115                 120                 125

Lys Gly Leu Gln Gly Phe Leu Met Thr His Ser Ile Gly Gly Gly Ser
130                 135                 140

Gly Ser Gly Leu Gly Ser Leu Ile Leu Glu Arg Leu Arg Gln Ala Tyr
145                 150                 155                 160

Pro Lys Lys Arg Ile Phe Thr Phe Ser Val Val Pro Ser Pro Leu Ile
                165                 170                 175

Ser Asp Ser Ala Val Glu Pro Tyr Asn Ala Ile Leu Thr Leu Gln Arg
            180                 185                 190

Ile Leu Asp Asn Ala Asp Gly Ala Val Leu Leu Asp Asn Glu Ala Leu
            195                 200                 205

Phe Arg Ile Ala Lys Ala Lys Leu Asn Arg Ser Pro Asn Tyr Met Asp
210                 215                 220

Leu Asn Asn Ile Ile Ala Leu Ile Val Ser Ser Val Thr Ala Ser Leu
225                 230                 235                 240

Arg Phe Pro Gly Lys Leu Asn Thr Asp Leu Ser Glu Phe Val Thr Asn
                245                 250                 255

Leu Val Pro Phe Pro Gly Asn His Phe Leu Thr Ala Ser Phe Ala Pro
            260                 265                 270
```

```
Met Arg Gly Ala Gly Gln Glu Gly Gln Val Arg Thr Asn Phe Pro Asp
            275                 280                 285

Leu Ala Arg Glu Thr Phe Ala Gln Asp Asn Phe Thr Ala Ala Ile Asp
            290                 295                 300

Trp Gln Gln Gly Val Tyr Leu Ala Ala Ser Leu Phe Arg Gly Asp
305                 310                 315                 320

Val Lys Ala Lys Asp Val Asp Glu Asn Met Ala Thr Ile Arg Lys Ser
                325                 330                 335

Leu Asn Tyr Ala Ser Tyr Met Pro Ala Ser Gly Gly Leu Lys Leu Gly
            340                 345                 350

Tyr Ala Glu Thr Ala Pro Glu Gly Phe Ala Ser Ser Gly Leu Ala Leu
            355                 360                 365

Val Asn His Thr Gly Ile Ala Ala Val Phe Glu Arg Leu Ile Ala Gln
            370                 375                 380

Phe Asp Ile Met Phe Asp Asn His Ala Tyr Thr His Trp Tyr Glu Asn
385                 390                 395                 400

Ala Gly Val Ser Arg Asp Met Met Ala Lys Ala Arg Asn Gln Ile Ala
                405                 410                 415

Thr Leu Ala Gln Ser Tyr Arg Asp Ala Ser
            420                 425

<210> SEQ ID NO 3
<211> LENGTH: 471
<212> TYPE: PRT
<213> ORGANISM: Prosthecobacter vanneervenii

<400> SEQUENCE: 3

Met Lys Val Asn Asn Thr Ile Val Ile Ser Ile Gly Gln Ala Gly Asn
1               5                   10                  15

Gln Ile Ala Ala Ser Phe Trp Lys Thr Ile Cys Gln Glu His Gly Ile
            20                  25                  30

Asp Pro Met Thr Gly Gln Thr Ala Gln Gly Gln Ala Pro Arg Gly Asn
            35                  40                  45

Trp Ser Ala Phe Phe Thr Lys Leu Gly Glu Ser Thr Ser Gly Ser Tyr
50                  55                  60

Val Pro Arg Ala Val Met Val Asp Leu Glu Pro Ser Val Ile Asp Asn
65                  70                  75                  80

Ile Lys Ala Thr Ser Gly Ser Leu Phe Asn Pro Gly Asn Leu Ile Ser
                85                  90                  95

Arg Thr Glu Gly Ala Gly Gly Asn Phe Ala Val Gly Tyr Leu Gly Ala
            100                 105                 110

Gly Arg Glu Val Leu Pro Glu Val Met Ser Arg Leu Asp Ser Glu Ile
            115                 120                 125

Asp Lys Cys Asp Asn Val Gly Gly Ile Ile Val Leu His Ala Thr Gly
130                 135                 140

Gly Gly Ser Gly Ser Gly Phe Gly Ala Leu Leu Ile Glu Ser Ile Lys
145                 150                 155                 160

Glu Lys Tyr Pro Glu Phe Pro Val Leu Ser Cys Ala Val Leu Pro Ser
                165                 170                 175

Pro Gln Val Ser Ser Val Val Thr Glu Pro Tyr Asn Thr Val Phe Thr
            180                 185                 190

Leu Asn Thr Leu Arg Arg Ala Ala Asp Ala Cys Leu Ile Phe Asp Asn
            195                 200                 205

Glu Ala Leu Phe Glu Leu Ala His Arg Lys Trp Asn Ile Glu Ser Pro
210                 215                 220
```

```
Thr Val Asp Asp Leu Asn Leu Leu Ile Thr Glu Ala Leu Ala Gly Leu
225                 230                 235                 240

Thr Ala Ser Met Arg Phe Ser Gly Phe Leu Thr Val Glu Ile Ser Leu
            245                 250                 255

Arg Glu Leu Leu Thr Asn Leu Val Pro Gln Pro Ser Leu His Phe Leu
        260                 265                 270

Met Cys Ser Phe Ala Pro Leu Thr Pro Pro Asp Arg Ser Lys Phe Glu
    275                 280                 285

Glu Met Gly Val Glu Glu Met Ile Arg Ser Leu Phe Asp Asn Gly Ser
290                 295                 300

Val Phe Ala Ala Cys Ser Pro Met Glu Gly Arg Phe Leu Ser Thr Ala
305                 310                 315                 320

Val Leu Tyr Arg Gly Ile Met Glu Asp Lys Pro Leu Ala Asp Ser Ala
            325                 330                 335

Leu Ala Ala Met Arg Glu Gln Leu Pro Leu Thr Tyr Trp Ile Pro Thr
        340                 345                 350

Ala Phe Lys Ile Gly Tyr Val Glu Gln Ala Gly Ile Ser His Arg Lys
    355                 360                 365

Ser Met Val Leu Leu Ala Asn Asn Thr Glu Ile Ala Arg Val Leu Asp
370                 375                 380

Arg Ile Cys His Asn Phe Asp Lys Leu Trp Gln Arg Lys Ala Phe Ala
385                 390                 395                 400

Asn Trp Tyr Leu Asn Glu Gly Met Ser Glu Glu Gln Ile Asn Ala Leu
            405                 410                 415

Arg Ala Ser Ala Gln Glu Leu Ile Gln Ser Tyr Gln Val Ala Glu Glu
        420                 425                 430

Ser Gly Ala Lys Ala Lys Val Gln Asp Ser Ser Ala Asp Tyr Pro Arg
    435                 440                 445

Ser Ser Ala Ser Ser Asp Asp Ser Arg Ser Gly Met Ser Leu Arg Asp
450                 455                 460

Leu Val Asp Arg Arg Ala
465                 470

<210> SEQ ID NO 4
<211> LENGTH: 424
<212> TYPE: PRT
<213> ORGANISM: Prosthecobacter vanneervenii

<400> SEQUENCE: 4

Met Arg Glu Ile Leu Ser Ile His Val Gly Gln Cys Gly Asn Gln Ile
1               5                   10                  15

Ala Asp Arg Phe Trp Arg Leu Val Leu Arg Glu His Gly Leu Thr Glu
            20                  25                  30

Ala Gly Thr Pro Lys Glu Gly Thr Asn Val Ala Ala Asn Ala Asn Met
        35                  40                  45

Glu Val Phe Phe His Lys Val Arg Asp Gly Lys Tyr Ile Pro Arg Ala
    50                  55                  60

Ile Leu Val Asp Leu Glu Pro Gly Val Ile Ala Arg Ile Glu Gly Gly
65                  70                  75                  80

Asp Met Ala Gln Leu Phe Asp Glu Ser Cys Ile Ile Arg Lys Ile Pro
            85                  90                  95

Gly Ala Ala Asn Asn Trp Ala Arg Gly Tyr Asn Val Glu Gly Glu Arg
        100                 105                 110

Ile Ile Asp Gln Ile Met Asn Val Ile Asp Ala Ala Val Glu Lys Thr
    115                 120                 125
```

-continued

```
Lys Ser Leu Gln Gly Phe Leu Leu Thr His Ser Ile Gly Gly Gly Ser
    130                 135                 140

Gly Ser Gly Leu Gly Ser Leu Ile Leu Glu Arg Leu Arg Gln Ala Tyr
145                 150                 155                 160

Pro Lys Lys Arg Ile Phe Thr Phe Ser Val Ala Pro Ser Pro Leu Ile
                165                 170                 175

Ser Asp Ser Ala Val Glu Pro Tyr Asn Ala Ile Leu Thr Leu Gln Arg
            180                 185                 190

Ile Leu Asp Asn Ala Asp Ala Val Leu Leu Asp Asn Glu Ala Leu
        195                 200                 205

Phe Arg Ile Ala Lys Ser Lys Leu His Arg Ser Pro Asn Tyr Met Asp
210                 215                 220

Leu Asn His Ile Ile Ala Leu Ile Met Ser Ser Val Thr Ala Ser Leu
225                 230                 235                 240

Arg Phe Pro Gly Lys Leu Asn Thr Asp Leu Gly Glu Tyr Val Thr Asn
                245                 250                 255

Leu Val Pro Phe Pro Gly Asn His Phe Leu Thr Ala Ser Phe Ala Pro
            260                 265                 270

Met Arg Ala Pro Gly Gln Glu Gly Gln Val Arg Ile Asn Phe Pro Asp
        275                 280                 285

Ile Ala Arg Glu Thr Phe Ala Gln Asp Asn Phe Thr Ala Ala Ile Asp
290                 295                 300

Trp Thr Asn Gly Val Tyr Leu Ser Ala Cys Ala Leu Phe Arg Gly Asp
305                 310                 315                 320

Val Lys Ala Lys Glu Val Glu Asn Met Ala Ala Ile Arg Lys Ser
                325                 330                 335

Leu Asn Phe Ala Ser Tyr Val Pro Thr Gly Val Lys Leu Gly Val Ala
            340                 345                 350

Glu Thr Ala Pro Glu Gly Phe Ala Ser Ser Gly Leu Ala Leu Val Asn
        355                 360                 365

His Thr Gly Ile Ala Ala Val Phe Glu Arg Leu Ile Asn Asn Phe Asp
370                 375                 380

Ile Met Phe Asp Asn His Ala Tyr Thr His Trp Tyr Glu Asn Asn Gly
385                 390                 395                 400

Val Ser Arg Asp Met Met Ala His Ala Arg Asn Thr Ile Val Asn Leu
                405                 410                 415

Ala Gln Ser Tyr Arg Asp Ala Ser
            420

<210> SEQ ID NO 5
<211> LENGTH: 470
<212> TYPE: PRT
<213> ORGANISM: Prosthecobacter debontii

<400> SEQUENCE: 5

Met Lys Val Asn Asn Thr Ile Val Val Ser Ile Gly Gln Ala Gly Asn
1               5                   10                  15

Gln Ile Ala Ala Ser Phe Trp Lys Thr Ile Cys Gln Glu His Gly Ile
            20                  25                  30

Asp Pro Leu Thr Gly Gln Thr Ala Gly Gly Ala Thr Pro Arg Gly Asn
        35                  40                  45

Trp Ser Ala Phe Phe Ser Ser Leu Gly Asp Ser Gly Gly Gly Ser Phe
    50                  55                  60

Val Pro Arg Ala Val Met Val Asp Leu Glu Pro Ser Val Ile Asn Gln
65                  70                  75                  80
```

Val Lys Ser Thr Ser Gly Ser Leu Phe Asn Pro Ala Asn Leu Ile Ser
                85                  90                  95

Arg Thr Glu Gly Ala Gly Gly Asn Phe Ala Val Gly Tyr Leu Gly Ala
            100                 105                 110

Gly Arg Glu Val Leu Pro Glu Val Met Ser Arg Leu Asp Phe Glu Ile
            115                 120                 125

Asp Lys Cys Asp Asn Val Gly Gly Ile Ile Val Leu His Ala Ile Gly
130                 135                 140

Gly Gly Ser Gly Ser Gly Leu Gly Cys Leu Leu Ile Glu Ser Leu Lys
145                 150                 155                 160

Glu Lys Tyr Pro Glu Tyr Pro Val Leu Ser Cys Ala Val Leu Pro Ser
                165                 170                 175

Pro Gln Val Ser Ser Val Val Thr Glu Pro Tyr Asn Thr Val Phe Ala
            180                 185                 190

Leu Asn Thr Leu Arg Arg Ala Ala Asp Ala Cys Leu Ile Phe Asp Asn
            195                 200                 205

Glu Ala Leu Phe Asp Leu Ala His Arg Lys Trp Asn Ile Glu Ser Pro
210                 215                 220

Thr Val Asp Asp Leu Asn Leu Leu Ile Thr Glu Ala Leu Ala Gly Ile
225                 230                 235                 240

Thr Ala Ser Met Arg Phe Ser Gly Phe Leu Thr Val Glu Ile Ser Leu
                245                 250                 255

Arg Glu Leu Leu Thr Asn Leu Val Pro Gln Pro Ser Leu His Phe Leu
            260                 265                 270

Met Cys Ala Phe Ala Pro Leu Thr Ala Pro Asp Arg Ser Lys Phe Glu
            275                 280                 285

Glu Met Gly Ile Glu Asp Met Ile Arg Ser Leu Phe Asp Asn Asp Ser
290                 295                 300

Val Tyr Ala Ala Cys Ser Pro Met Glu Gly Arg Phe Leu Ser Thr Ala
305                 310                 315                 320

Val Leu Tyr Arg Gly Ile Met Glu Asp Lys Pro Leu Ala Asp Ala Ala
                325                 330                 335

Leu Ala Ala Met Arg Glu Lys Leu Pro Leu Thr Tyr Trp Ile Pro Thr
            340                 345                 350

Ala Phe Lys Ile Gly Tyr Val Glu Gln Ser Gly Ile Ser His Arg Lys
            355                 360                 365

Ser Met Val Leu Leu Ala Asn Asn Thr Glu Ile Ala Arg Val Leu Asp
370                 375                 380

Arg Ile Cys His Asn Phe Asp Lys Leu Trp Gln Lys Ala Phe Ala
385                 390                 395                 400

Asn Trp Tyr Leu Asn Glu Gly Met Ser Glu Gln Ile Asn Gly Leu
                405                 410                 415

Arg Ala Ser Ala Gln Glu Leu Ile Gln Ser Tyr Gln Val Ala Glu Glu
            420                 425                 430

Ser Gly Ala Lys Ala Lys Ile Gln Asp Val Ser Gly Glu Thr Val Ser
            435                 440                 445

Arg Ser Ser Ser Met Asp Asp Pro Arg Ser Thr Met Ser Leu Arg Asp
450                 455                 460

Leu Val Glu Arg Arg
465                 470

<210> SEQ ID NO 6
<211> LENGTH: 426
<212> TYPE: PRT

<213> ORGANISM: Prosthecobacter debontii
<220> FEATURE:
<221> NAME/KEY: misc_feature
<222> LOCATION: (214)..(214)
<223> OTHER INFORMATION: Xaa can be any naturally occurring amino acid

<400> SEQUENCE: 6

```
Met Arg Glu Ile Leu Ser Ile His Val Gly Gln Cys Gly Asn Gln Ile
1               5                   10                  15

Ala Asp Ser Phe Trp Arg Leu Ala Leu Lys Glu His Gly Leu Thr Glu
            20                  25                  30

Thr Gly Thr Leu Lys Glu Gly Ala Asn Ala Ala Ala Asn Ser Asp Leu
        35                  40                  45

Glu Val Phe Phe His Arg Val Arg Glu Gly Lys Tyr Val Pro Arg Ala
    50                  55                  60

Val Leu Ile Asp Leu Glu Pro Gly Val Ile Gly Arg Ile Glu Ser Gly
65                  70                  75                  80

Asp Met Ser Lys Leu Phe Asp Glu Ser Cys Ile Val Arg Lys Ile Pro
                85                  90                  95

Gly Ala Ala Asn Asn Trp Ala Arg Gly Tyr His Ala Glu Gly Lys Arg
            100                 105                 110

Val Ile Asp Gln Ile Met Asn Val Ile Asp Ser Ala Val Glu Lys Thr
        115                 120                 125

Lys Gly Leu Gln Gly Phe Leu Leu Thr His Ser Ile Gly Gly Gly Ser
130                 135                 140

Gly Ser Gly Leu Gly Ser Leu Ile Leu Glu Arg Leu Arg Gln Ala Tyr
145                 150                 155                 160

Pro Lys Lys Arg Ile Phe Thr Phe Ser Val Val Pro Ser Pro Leu Ile
                165                 170                 175

Ser Asp Ser Ala Val Glu Pro Tyr Asn Ala Ile Leu Thr Leu Lys Arg
            180                 185                 190

Leu Leu Asp His Ala Asp Gly Ser Val Leu Leu Asp Asn Glu Ala Leu
        195                 200                 205

Phe Arg Ile Ala Lys Xaa Lys Leu Asn Arg Ser Pro Thr Tyr Met Asp
    210                 215                 220

Leu Asn Asn Ile Ile Ala Leu Ile Val Ser Ser Val Thr Ala Ser Leu
225                 230                 235                 240

Arg Phe Pro Gly Lys Leu Asn Thr Asp Leu Ser Glu Phe Val Thr Asn
                245                 250                 255

Leu Val Pro Phe Pro Gly Asn His Phe Leu Thr Ala Ser Phe Ala Pro
            260                 265                 270

Met Arg Thr Ala Asp Asp Glu Ser Gln Val Arg Met Ser Phe Pro Glu
        275                 280                 285

Leu Ala Arg Glu Thr Phe Ala Gln Asp Asn Phe Thr Ala Glu Ile Asp
    290                 295                 300

Trp Gln Asn Gly Val Tyr Leu Ala Ser Ala Leu Phe Arg Gly Glu
305                 310                 315                 320

Val Lys Ala Lys Glu Val Asp Glu Asn Met Ala Thr Ile Arg Lys Glu
                325                 330                 335

Leu Asn Tyr Ala Ser Tyr Met Pro Ala Ser Gly Gly Leu Lys Leu Gly
            340                 345                 350

Tyr Ala Glu Thr Ala Pro Ala Gly Phe Ala Ser Ser Gly Leu Ala Leu
        355                 360                 365

Val Asn His Thr Gly Ile Ser Ala Val Phe Glu Arg Leu Ile Gly Gln
    370                 375                 380
```

-continued

```
Phe Asp Ile Met Phe Asp Asn His Ala Tyr Thr His Trp Tyr Glu Asn
385                 390                 395                 400

Ala Gly Val Ser Arg Asp Gln Met Ala Val Ala Arg Asp Gln Ile Ala
                405                 410                 415

Asn Leu Ala Leu Ser Tyr Arg Asp Ala Ser
            420                 425

<210> SEQ ID NO 7
<211> LENGTH: 473
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (9)..(9)
<223> OTHER INFORMATION: Xaa denotes any amino acid residue
<220> FEATURE:
<221> NAME/KEY: MISC_FEATURE
<222> LOCATION: (26)..(26)
<223> OTHER INFORMATION: Xaa denotes any amino acid residue
<220> FEATURE:
<221> NAME/KEY: MISC_FEATURE
<222> LOCATION: (28)..(28)
<223> OTHER INFORMATION: Xaa denotes any amino acid residue
<220> FEATURE:
<221> NAME/KEY: MISC_FEATURE
<222> LOCATION: (35)..(35)
<223> OTHER INFORMATION: Xaa denotes any amino acid residue
<220> FEATURE:
<221> NAME/KEY: MISC_FEATURE
<222> LOCATION: (41)..(41)
<223> OTHER INFORMATION: Xaa denotes any amino acid residue
<220> FEATURE:
<221> NAME/KEY: MISC_FEATURE
<222> LOCATION: (43)..(44)
<223> OTHER INFORMATION: Xaa denotes any amino acid residue
<220> FEATURE:
<221> NAME/KEY: MISC_FEATURE
<222> LOCATION: (51)..(51)
<223> OTHER INFORMATION: Xaa denotes any amino acid residue
<220> FEATURE:
<221> NAME/KEY: MISC_FEATURE
<222> LOCATION: (54)..(55)
<223> OTHER INFORMATION: Xaa denotes any amino acid residue
<220> FEATURE:
<221> NAME/KEY: MISC_FEATURE
<222> LOCATION: (58)..(58)
<223> OTHER INFORMATION: Xaa denotes any amino acid residue
<220> FEATURE:
<221> NAME/KEY: MISC_FEATURE
<222> LOCATION: (60)..(61)
<223> OTHER INFORMATION: Xaa denotes any amino acid residue
<220> FEATURE:
<221> NAME/KEY: MISC_FEATURE
<222> LOCATION: (64)..(64)
<223> OTHER INFORMATION: Xaa denotes any amino acid residue
<220> FEATURE:
<221> NAME/KEY: MISC_FEATURE
<222> LOCATION: (69)..(69)
<223> OTHER INFORMATION: Xaa denotes any amino acid residue
<220> FEATURE:
<221> NAME/KEY: MISC_FEATURE
<222> LOCATION: (79)..(81)
<223> OTHER INFORMATION: Xaa denotes any amino acid residue
<220> FEATURE:
<221> NAME/KEY: MISC_FEATURE
<222> LOCATION: (83)..(83)
<223> OTHER INFORMATION: Xaa denotes any amino acid residue
<220> FEATURE:
<221> NAME/KEY: MISC_FEATURE
<222> LOCATION: (92)..(92)
<223> OTHER INFORMATION: Xaa denotes any amino acid residue
<220> FEATURE:
<221> NAME/KEY: MISC_FEATURE
<222> LOCATION: (126)..(126)
<223> OTHER INFORMATION: Xaa denotes any amino acid residue
```

```
-continued

<220> FEATURE:
<221> NAME/KEY: MISC_FEATURE
<222> LOCATION: (143)..(143)
<223> OTHER INFORMATION: Xaa denotes any amino acid residue
<220> FEATURE:
<221> NAME/KEY: MISC_FEATURE
<222> LOCATION: (147)..(147)
<223> OTHER INFORMATION: Xaa denotes any amino acid residue
<220> FEATURE:
<221> NAME/KEY: MISC_FEATURE
<222> LOCATION: (151)..(151)
<223> OTHER INFORMATION: Xaa denotes any amino acid residue
<220> FEATURE:
<221> NAME/KEY: MISC_FEATURE
<222> LOCATION: (153)..(153)
<223> OTHER INFORMATION: Xaa denotes any amino acid residue
<220> FEATURE:
<221> NAME/KEY: MISC_FEATURE
<222> LOCATION: (159)..(159)
<223> OTHER INFORMATION: Xaa denotes any amino acid residue
<220> FEATURE:
<221> NAME/KEY: MISC_FEATURE
<222> LOCATION: (164)..(164)
<223> OTHER INFORMATION: Xaa denotes any amino acid residue
<220> FEATURE:
<221> NAME/KEY: MISC_FEATURE
<222> LOCATION: (166)..(166)
<223> OTHER INFORMATION: Xaa denotes any amino acid residue
<220> FEATURE:
<221> NAME/KEY: MISC_FEATURE
<222> LOCATION: (192)..(192)
<223> OTHER INFORMATION: Xaa denotes any amino acid residue
<220> FEATURE:
<221> NAME/KEY: MISC_FEATURE
<222> LOCATION: (199)..(199)
<223> OTHER INFORMATION: Xaa denotes any amino acid residue
<220> FEATURE:
<221> NAME/KEY: MISC_FEATURE
<222> LOCATION: (213)..(213)
<223> OTHER INFORMATION: Xaa denotes any amino acid residue
<220> FEATURE:
<221> NAME/KEY: MISC_FEATURE
<222> LOCATION: (240)..(240)
<223> OTHER INFORMATION: Xaa denotes any amino acid residue
<220> FEATURE:
<221> NAME/KEY: MISC_FEATURE
<222> LOCATION: (255)..(255)
<223> OTHER INFORMATION: Xaa denotes any amino acid residue
<220> FEATURE:
<221> NAME/KEY: MISC_FEATURE
<222> LOCATION: (275)..(275)
<223> OTHER INFORMATION: Xaa denotes any amino acid residue
<220> FEATURE:
<221> NAME/KEY: MISC_FEATURE
<222> LOCATION: (281)..(281)
<223> OTHER INFORMATION: Xaa denotes any amino acid residue
<220> FEATURE:
<221> NAME/KEY: MISC_FEATURE
<222> LOCATION: (290)..(290)
<223> OTHER INFORMATION: Xaa denotes any amino acid residue
<220> FEATURE:
<221> NAME/KEY: MISC_FEATURE
<222> LOCATION: (292)..(292)
<223> OTHER INFORMATION: Xaa denotes any amino acid residue
<220> FEATURE:
<221> NAME/KEY: MISC_FEATURE
<222> LOCATION: (294)..(294)
<223> OTHER INFORMATION: Xaa denotes any amino acid residue
<220> FEATURE:
<221> NAME/KEY: MISC_FEATURE
<222> LOCATION: (297)..(297)
<223> OTHER INFORMATION: Xaa denotes any amino acid residue
<220> FEATURE:
<221> NAME/KEY: MISC_FEATURE
<222> LOCATION: (303)..(303)
<223> OTHER INFORMATION: Xaa denotes any amino acid residue
<220> FEATURE:
<221> NAME/KEY: MISC_FEATURE
<222> LOCATION: (306)..(306)
<223> OTHER INFORMATION: Xaa denotes any amino acid residue
```

```
<220> FEATURE:
<221> NAME/KEY: MISC_FEATURE
<222> LOCATION: (335)..(335)
<223> OTHER INFORMATION: Xaa denotes any amino acid residue
<220> FEATURE:
<221> NAME/KEY: MISC_FEATURE
<222> LOCATION: (343)..(343)
<223> OTHER INFORMATION: Xaa denotes any amino acid residue
<220> FEATURE:
<221> NAME/KEY: MISC_FEATURE
<222> LOCATION: (362)..(362)
<223> OTHER INFORMATION: Xaa denotes any amino acid residue
<220> FEATURE:
<221> NAME/KEY: MISC_FEATURE
<222> LOCATION: (415)..(415)
<223> OTHER INFORMATION: Xaa denotes any amino acid residue
<220> FEATURE:
<221> NAME/KEY: MISC_FEATURE
<222> LOCATION: (424)..(424)
<223> OTHER INFORMATION: Xaa denotes any amino acid residue
<220> FEATURE:
<221> NAME/KEY: MISC_FEATURE
<222> LOCATION: (439)..(439)
<223> OTHER INFORMATION: Xaa denotes any amino acid residue
<220> FEATURE:
<221> NAME/KEY: MISC_FEATURE
<222> LOCATION: (442)..(448)
<223> OTHER INFORMATION: Xaa denotes any amino acid residue
<220> FEATURE:
<221> NAME/KEY: MISC_FEATURE
<222> LOCATION: (450)..(456)
<223> OTHER INFORMATION: Xaa denotes any amino acid residue
<220> FEATURE:
<221> NAME/KEY: MISC_FEATURE
<222> LOCATION: (459)..(459)
<223> OTHER INFORMATION: Xaa denotes any amino acid residue
<220> FEATURE:
<221> NAME/KEY: MISC_FEATURE
<222> LOCATION: (461)..(462)
<223> OTHER INFORMATION: Xaa denotes any amino acid residue
<220> FEATURE:
<221> NAME/KEY: MISC_FEATURE
<222> LOCATION: (470)..(470)
<223> OTHER INFORMATION: Xaa denotes any amino acid residue

<400> SEQUENCE: 7

Met Lys Val Asn Asn Thr Ile Val Xaa Ser Ile Gly Gln Ala Gly Asn
1               5                   10                  15

Gln Ile Ala Ala Ser Phe Trp Lys Thr Xaa Cys Xaa Glu His Gly Ile
            20                  25                  30

Asp Pro Xaa Thr Gly Gln Thr Ala Xaa Gly Xaa Xaa Pro Arg Gly Asn
        35                  40                  45

Trp Ser Xaa Phe Phe Xaa Xaa Leu Gly Xaa Ser Xaa Xaa Gly Ser Xaa
    50                  55                  60

Val Pro Arg Ala Xaa Met Val Asp Leu Glu Pro Ser Val Ile Xaa Xaa
65                  70                  75                  80

Xaa Lys Xaa Thr Ser Gly Ser Leu Phe Asn Pro Xaa Asn Leu Ile Ser
                85                  90                  95

Arg Thr Glu Gly Ala Gly Gly Asn Phe Ala Val Gly Tyr Leu Gly Ala
            100                 105                 110

Gly Arg Glu Val Leu Pro Glu Val Met Ser Arg Leu Asp Xaa Glu Ile
        115                 120                 125

Asp Lys Cys Asp Asn Val Gly Ile Ile Val Leu His Ala Xaa Gly
    130                 135                 140

Gly Gly Xaa Gly Ser Gly Xaa Gly Xaa Leu Leu Ile Glu Ser Xaa Lys
145                 150                 155                 160

Glu Lys Tyr Xaa Glu Xaa Pro Val Leu Ser Cys Ala Val Leu Pro Ser
                165                 170                 175
```

```
Pro Gln Val Ser Ser Val Val Thr Glu Pro Tyr Asn Thr Val Phe Xaa
            180                 185                 190

Leu Asn Thr Leu Arg Arg Xaa Ala Asp Ala Cys Leu Ile Phe Asp Asn
            195                 200                 205

Glu Ala Leu Phe Xaa Leu Ala His Arg Lys Trp Asn Ile Glu Ser Pro
            210                 215                 220

Thr Val Asp Asp Leu Asn Leu Leu Ile Thr Glu Ala Leu Ala Gly Xaa
225                 230                 235                 240

Thr Ala Ser Met Arg Phe Ser Gly Phe Leu Thr Val Glu Ile Xaa Leu
                245                 250                 255

Arg Glu Leu Leu Thr Asn Leu Val Pro Gln Pro Ser Leu His Phe Leu
            260                 265                 270

Met Cys Xaa Phe Ala Pro Leu Thr Xaa Pro Asp Arg Ser Lys Phe Glu
            275                 280                 285

Glu Xaa Gly Xaa Glu Xaa Met Ile Xaa Ser Leu Phe Asp Asn Xaa Ser
            290                 295                 300

Val Xaa Ala Ala Cys Ser Pro Met Glu Gly Arg Phe Leu Ser Thr Ala
305                 310                 315                 320

Val Leu Tyr Arg Gly Ile Met Glu Asp Lys Pro Leu Ala Asp Xaa Ala
                325                 330                 335

Leu Ala Ala Met Arg Glu Xaa Leu Pro Leu Thr Tyr Trp Ile Pro Thr
                340                 345                 350

Ala Phe Lys Ile Gly Tyr Val Glu Gln Xaa Gly Ile Ser His Arg Lys
                355                 360                 365

Ser Met Val Leu Leu Ala Asn Asn Thr Glu Ile Ala Arg Val Leu Asp
            370                 375                 380

Arg Ile Cys His Asn Phe Asp Lys Leu Trp Gln Arg Lys Ala Phe Ala
385                 390                 395                 400

Asn Trp Tyr Leu Asn Glu Gly Met Ser Glu Glu Gln Ile Asn Xaa Leu
                405                 410                 415

Arg Ala Ser Ala Gln Glu Leu Xaa Gln Ser Tyr Gln Val Ala Glu Glu
            420                 425                 430

Ser Gly Ala Lys Ala Lys Xaa Gln Asp Xaa Xaa Xaa Xaa Xaa Xaa
            435                 440                 445

Arg Xaa Xaa Xaa Xaa Xaa Xaa Xaa Asp Asp Xaa Arg Xaa Xaa Met Ser
450                 455                 460

Leu Arg Asp Leu Val Xaa Arg Arg
465                 470

<210> SEQ ID NO 8
<211> LENGTH: 426
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa denotes any amino acid residue
<220> FEATURE:
<221> NAME/KEY: MISC_FEATURE
<222> LOCATION: (19)..(19)
<223> OTHER INFORMATION: Xaa denotes any amino acid residue
<220> FEATURE:
<221> NAME/KEY: MISC_FEATURE
<222> LOCATION: (24)..(24)
<223> OTHER INFORMATION: Xaa denotes any amino acid residue
<220> FEATURE:
<221> NAME/KEY: MISC_FEATURE
<222> LOCATION: (26)..(26)
<223> OTHER INFORMATION: Xaa denotes any amino acid residue
```

```
<220> FEATURE:
<221> NAME/KEY: MISC_FEATURE
<222> LOCATION: (33)..(33)
<223> OTHER INFORMATION: Xaa denotes any amino acid residue
<220> FEATURE:
<221> NAME/KEY: MISC_FEATURE
<222> LOCATION: (36)..(36)
<223> OTHER INFORMATION: Xaa denotes any amino acid residue
<220> FEATURE:
<221> NAME/KEY: MISC_FEATURE
<222> LOCATION: (40)..(40)
<223> OTHER INFORMATION: Xaa denotes any amino acid residue
<220> FEATURE:
<221> NAME/KEY: MISC_FEATURE
<222> LOCATION: (42)..(42)
<223> OTHER INFORMATION: Xaa denotes any amino acid residue
<220> FEATURE:
<221> NAME/KEY: MISC_FEATURE
<222> LOCATION: (46)..(48)
<223> OTHER INFORMATION: Xaa denotes any amino acid residue
<220> FEATURE:
<221> NAME/KEY: MISC_FEATURE
<222> LOCATION: (54)..(54)
<223> OTHER INFORMATION: Xaa denotes any amino acid residue
<220> FEATURE:
<221> NAME/KEY: MISC_FEATURE
<222> LOCATION: (57)..(57)
<223> OTHER INFORMATION: Xaa denotes any amino acid residue
<220> FEATURE:
<221> NAME/KEY: MISC_FEATURE
<222> LOCATION: (61)..(61)
<223> OTHER INFORMATION: Xaa denotes any amino acid residue
<220> FEATURE:
<221> NAME/KEY: MISC_FEATURE
<222> LOCATION: (65)..(65)
<223> OTHER INFORMATION: Xaa denotes any amino acid residue
<220> FEATURE:
<221> NAME/KEY: MISC_FEATURE
<222> LOCATION: (67)..(67)
<223> OTHER INFORMATION: Xaa denotes any amino acid residue
<220> FEATURE:
<221> NAME/KEY: MISC_FEATURE
<222> LOCATION: (75)..(75)
<223> OTHER INFORMATION: Xaa denotes any amino acid residue
<220> FEATURE:
<221> NAME/KEY: MISC_FEATURE
<222> LOCATION: (79)..(79)
<223> OTHER INFORMATION: Xaa denotes any amino acid residue
<220> FEATURE:
<221> NAME/KEY: MISC_FEATURE
<222> LOCATION: (83)..(84)
<223> OTHER INFORMATION: Xaa denotes any amino acid residue
<220> FEATURE:
<221> NAME/KEY: MISC_FEATURE
<222> LOCATION: (90)..(90)
<223> OTHER INFORMATION: Xaa denotes any amino acid residue
<220> FEATURE:
<221> NAME/KEY: MISC_FEATURE
<222> LOCATION: (92)..(92)
<223> OTHER INFORMATION: Xaa denotes any amino acid residue
<220> FEATURE:
<221> NAME/KEY: MISC_FEATURE
<222> LOCATION: (107)..(108)
<223> OTHER INFORMATION: Xaa denotes any amino acid residue
<220> FEATURE:
<221> NAME/KEY: MISC_FEATURE
<222> LOCATION: (111)..(113)
<223> OTHER INFORMATION: Xaa denotes any amino acid residue
<220> FEATURE:
<221> NAME/KEY: MISC_FEATURE
<222> LOCATION: (123)..(123)
<223> OTHER INFORMATION: Xaa denotes any amino acid residue
<220> FEATURE:
<221> NAME/KEY: MISC_FEATURE
<222> LOCATION: (130)..(130)
<223> OTHER INFORMATION: Xaa denotes any amino acid residue
<220> FEATURE:
<221> NAME/KEY: MISC_FEATURE
<222> LOCATION: (136)..(136)
<223> OTHER INFORMATION: Xaa denotes any amino acid residue
```

```
<220> FEATURE:
<221> NAME/KEY: MISC_FEATURE
<222> LOCATION: (171)..(171)
<223> OTHER INFORMATION: Xaa denotes any amino acid residue
<220> FEATURE:
<221> NAME/KEY: MISC_FEATURE
<222> LOCATION: (191)..(191)
<223> OTHER INFORMATION: Xaa denotes any amino acid residue
<220> FEATURE:
<221> NAME/KEY: MISC_FEATURE
<222> LOCATION: (193)..(193)
<223> OTHER INFORMATION: Xaa denotes any amino acid residue
<220> FEATURE:
<221> NAME/KEY: MISC_FEATURE
<222> LOCATION: (199)..(200)
<223> OTHER INFORMATION: Xaa denotes any amino acid residue
<220> FEATURE:
<221> NAME/KEY: MISC_FEATURE
<222> LOCATION: (214)..(214)
<223> OTHER INFORMATION: Xaa denotes any amino acid residue
<220> FEATURE:
<221> NAME/KEY: MISC_FEATURE
<222> LOCATION: (217)..(217)
<223> OTHER INFORMATION: Xaa denotes any amino acid residue
<220> FEATURE:
<221> NAME/KEY: MISC_FEATURE
<222> LOCATION: (221)..(221)
<223> OTHER INFORMATION: Xaa denotes any amino acid residue
<220> FEATURE:
<221> NAME/KEY: MISC_FEATURE
<222> LOCATION: (227)..(227)
<223> OTHER INFORMATION: Xaa denotes any amino acid residue
<220> FEATURE:
<221> NAME/KEY: MISC_FEATURE
<222> LOCATION: (233)..(233)
<223> OTHER INFORMATION: Xaa denotes any amino acid residue
<220> FEATURE:
<221> NAME/KEY: MISC_FEATURE
<222> LOCATION: (251)..(251)
<223> OTHER INFORMATION: Xaa denotes any amino acid residue
<220> FEATURE:
<221> NAME/KEY: MISC_FEATURE
<222> LOCATION: (253)..(253)
<223> OTHER INFORMATION: Xaa denotes any amino acid residue
<220> FEATURE:
<221> NAME/KEY: MISC_FEATURE
<222> LOCATION: (275)..(278)
<223> OTHER INFORMATION: Xaa denotes any amino acid residue
<220> FEATURE:
<221> NAME/KEY: MISC_FEATURE
<222> LOCATION: (280)..(280)
<223> OTHER INFORMATION: Xaa denotes any amino acid residue
<220> FEATURE:
<221> NAME/KEY: MISC_FEATURE
<222> LOCATION: (284)..(285)
<223> OTHER INFORMATION: Xaa denotes any amino acid residue
<220> FEATURE:
<221> NAME/KEY: MISC_FEATURE
<222> LOCATION: (288)..(289)
<223> OTHER INFORMATION: Xaa denotes any amino acid residue
<220> FEATURE:
<221> NAME/KEY: MISC_FEATURE
<222> LOCATION: (302)..(302)
<223> OTHER INFORMATION: Xaa denotes any amino acid residue
<220> FEATURE:
<221> NAME/KEY: MISC_FEATURE
<222> LOCATION: (306)..(307)
<223> OTHER INFORMATION: Xaa denotes any amino acid residue
<220> FEATURE:
<221> NAME/KEY: MISC_FEATURE
<222> LOCATION: (312)..(312)
<223> OTHER INFORMATION: Xaa denotes any amino acid residue
<220> FEATURE:
<221> NAME/KEY: MISC_FEATURE
<222> LOCATION: (314)..(314)
<223> OTHER INFORMATION: Xaa denotes any amino acid residue
<220> FEATURE:
<221> NAME/KEY: MISC_FEATURE
<222> LOCATION: (320)..(320)
<223> OTHER INFORMATION: Xaa denotes any amino acid residue
```

```
<220> FEATURE:
<221> NAME/KEY: MISC_FEATURE
<222> LOCATION: (325)..(325)
<223> OTHER INFORMATION: Xaa denotes any amino acid residue
<220> FEATURE:
<221> NAME/KEY: MISC_FEATURE
<222> LOCATION: (327)..(327)
<223> OTHER INFORMATION: Xaa denotes any amino acid residue
<220> FEATURE:
<221> NAME/KEY: MISC_FEATURE
<222> LOCATION: (332)..(332)
<223> OTHER INFORMATION: Xaa denotes any amino acid residue
<220> FEATURE:
<221> NAME/KEY: MISC_FEATURE
<222> LOCATION: (336)..(336)
<223> OTHER INFORMATION: Xaa denotes any amino acid residue
<220> FEATURE:
<221> NAME/KEY: MISC_FEATURE
<222> LOCATION: (339)..(339)
<223> OTHER INFORMATION: Xaa denotes any amino acid residue
<220> FEATURE:
<221> NAME/KEY: MISC_FEATURE
<222> LOCATION: (343)..(343)
<223> OTHER INFORMATION: Xaa denotes any amino acid residue
<220> FEATURE:
<221> NAME/KEY: MISC_FEATURE
<222> LOCATION: (345)..(346)
<223> OTHER INFORMATION: Xaa denotes any amino acid residue
<220> FEATURE:
<221> NAME/KEY: MISC_FEATURE
<222> LOCATION: (348)..(348)
<223> OTHER INFORMATION: Xaa denotes any amino acid residue
<220> FEATURE:
<221> NAME/KEY: MISC_FEATURE
<222> LOCATION: (352)..(352)
<223> OTHER INFORMATION: Xaa denotes any amino acid residue
<220> FEATURE:
<221> NAME/KEY: MISC_FEATURE
<222> LOCATION: (358)..(358)
<223> OTHER INFORMATION: Xaa denotes any amino acid residue
<220> FEATURE:
<221> NAME/KEY: MISC_FEATURE
<222> LOCATION: (360)..(360)
<223> OTHER INFORMATION: Xaa denotes any amino acid residue
<220> FEATURE:
<221> NAME/KEY: MISC_FEATURE
<222> LOCATION: (375)..(375)
<223> OTHER INFORMATION: Xaa denotes any amino acid residue
<220> FEATURE:
<221> NAME/KEY: MISC_FEATURE
<222> LOCATION: (383)..(384)
<223> OTHER INFORMATION: Xaa denotes any amino acid residue
<220> FEATURE:
<221> NAME/KEY: MISC_FEATURE
<222> LOCATION: (401)..(401)
<223> OTHER INFORMATION: Xaa denotes any amino acid residue
<220> FEATURE:
<221> NAME/KEY: MISC_FEATURE
<222> LOCATION: (407)..(407)
<223> OTHER INFORMATION: Xaa denotes any amino acid residue
<220> FEATURE:
<221> NAME/KEY: MISC_FEATURE
<222> LOCATION: (410)..(410)
<223> OTHER INFORMATION: Xaa denotes any amino acid residue
<220> FEATURE:
<221> NAME/KEY: MISC_FEATURE
<222> LOCATION: (413)..(414)
<223> OTHER INFORMATION: Xaa denotes any amino acid residue
<220> FEATURE:
<221> NAME/KEY: MISC_FEATURE
<222> LOCATION: (416)..(417)
<223> OTHER INFORMATION: Xaa denotes any amino acid residue
<220> FEATURE:
<221> NAME/KEY: MISC_FEATURE
<222> LOCATION: (420)..(420)
<223> OTHER INFORMATION: Xaa denotes any amino acid residue

<400> SEQUENCE: 8

Xaa Arg Glu Ile Leu Ser Ile His Val Gly Gln Cys Gly Asn Gln Ile
```

-continued

```
1               5                   10                  15
Ala Asp Xaa Phe Trp Arg Leu Xaa Leu Xaa Glu His Gly Leu Thr Glu
            20                  25                  30

Xaa Gly Thr Xaa Lys Glu Gly Xaa Asn Xaa Ala Ala Asn Xaa Xaa Xaa
            35                  40                  45

Glu Val Phe Phe His Xaa Val Arg Xaa Gly Lys Tyr Xaa Pro Arg Ala
            50                  55                  60

Xaa Leu Xaa Asp Leu Glu Pro Gly Val Ile Xaa Arg Ile Glu Xaa Gly
65                  70                  75                  80

Asp Met Xaa Xaa Leu Phe Asp Glu Ser Xaa Ile Xaa Arg Lys Ile Pro
            85                  90                  95

Gly Ala Ala Asn Asn Trp Ala Arg Gly Tyr Xaa Xaa Glu Gly Xaa Xaa
            100                 105                 110

Xaa Ile Asp Gln Ile Met Asn Val Ile Asp Xaa Ala Val Glu Lys Thr
            115                 120                 125

Lys Xaa Leu Gln Gly Phe Leu Xaa Thr His Ser Ile Gly Gly Gly Ser
            130                 135                 140

Gly Ser Gly Leu Gly Ser Leu Ile Leu Glu Arg Leu Arg Gln Ala Tyr
145                 150                 155                 160

Pro Lys Lys Arg Ile Phe Thr Phe Ser Val Xaa Pro Ser Pro Leu Ile
            165                 170                 175

Ser Asp Ser Ala Val Glu Pro Tyr Asn Ala Ile Leu Thr Leu Xaa Arg
            180                 185                 190

Xaa Leu Asp Asn Ala Asp Xaa Xaa Val Leu Leu Asp Asn Glu Ala Leu
            195                 200                 205

Phe Arg Ile Ala Lys Xaa Lys Leu Xaa Arg Ser Pro Xaa Tyr Met Asp
210                 215                 220

Leu Asn Xaa Asn Ile Ile Ala Leu Xaa Ser Ser Val Thr Ala Ser Leu
225                 230                 235                 240

Arg Phe Pro Gly Lys Leu Asn Thr Asp Leu Xaa Glu Xaa Val Thr Asn
            245                 250                 255

Leu Val Pro Phe Pro Gly Asn His Phe Leu Thr Ala Ser Phe Ala Pro
            260                 265                 270

Met Arg Xaa Xaa Xaa Xaa Glu Xaa Gln Val Arg Xaa Xaa Phe Pro Xaa
            275                 280                 285

Xaa Ala Arg Glu Thr Phe Ala Gln Asp Asn Phe Thr Ala Xaa Ile Asp
            290                 295                 300

Trp Xaa Xaa Gly Val Tyr Leu Xaa Ala Xaa Ala Leu Phe Arg Gly Xaa
305                 310                 315                 320

Val Lys Ala Lys Xaa Val Xaa Glu Asn Met Ala Xaa Ile Arg Lys Xaa
            325                 330                 335

Leu Asn Xaa Ala Ser Tyr Xaa Pro Xaa Xaa Gly Xaa Leu Lys Leu Xaa
            340                 345                 350

Tyr Ala Glu Thr Ala Xaa Glu Xaa Phe Ala Ser Ser Gly Leu Ala Leu
            355                 360                 365

Val Asn His Thr Gly Ile Xaa Ala Val Phe Glu Arg Leu Ile Xaa Xaa
            370                 375                 380

Phe Asp Ile Met Phe Asp Asn His Ala Tyr Thr His Trp Tyr Glu Asn
385                 390                 395                 400

Xaa Gly Val Ser Arg Asp Xaa Met Ala Xaa Ala Arg Xaa Xaa Ile Xaa
            405                 410                 415

Xaa Leu Ala Xaa Ser Tyr Arg Asp Ala Ser
            420                 425
```

```
<210> SEQ ID NO 9
<211> LENGTH: 15
<212> TYPE: PRT
<213> ORGANISM: Homo sapiens

<400> SEQUENCE: 9

Val Asp Ser Val Glu Gly Glu Gly Glu Glu Gly Glu Glu Tyr
1               5                   10                  15

<210> SEQ ID NO 10
<211> LENGTH: 13
<212> TYPE: PRT
<213> ORGANISM: Bos taurus

<400> SEQUENCE: 10

Ala Asp Ser Ala Glu Gly Asp Asp Glu Gly Asp Glu Tyr
1               5                   10

<210> SEQ ID NO 11
<211> LENGTH: 15
<212> TYPE: PRT
<213> ORGANISM: Rattus norvegicus

<400> SEQUENCE: 11

Val Gly Thr Asp Ser Phe Glu Glu Asn Glu Gly Glu Glu Phe
1               5                   10                  15

<210> SEQ ID NO 12
<211> LENGTH: 18
<212> TYPE: PRT
<213> ORGANISM: Gallus gallus

<400> SEQUENCE: 12

Ala Thr Ala Asp Glu Gln Gly Glu Phe Glu Glu Glu Gly Glu Glu Asp
1               5                   10                  15

Glu Ala

<210> SEQ ID NO 13
<211> LENGTH: 18
<212> TYPE: PRT
<213> ORGANISM: Bos taurus

<400> SEQUENCE: 13

Ala Thr Ala Asp Glu Gln Gly Glu Phe Glu Glu Glu Glu Gly Glu Asp
1               5                   10                  15

Glu Ala

<210> SEQ ID NO 14
<211> LENGTH: 18
<212> TYPE: PRT
<213> ORGANISM: Homo sapiens

<400> SEQUENCE: 14

Ala Thr Ala Glu Glu Glu Gly Glu Phe Glu Glu Glu Ala Glu Glu Glu
1               5                   10                  15

Val Ala

<210> SEQ ID NO 15
<211> LENGTH: 17
<212> TYPE: PRT
<213> ORGANISM: Danio rerio

<400> SEQUENCE: 15
```

-continued

```
Ala Thr Ala Glu Glu Glu Gly Glu Phe Glu Glu Glu Ala Glu Asp Asp
1               5                   10                  15
Ala
```

HYBRID PROKARYOTIC-EUKARYOTIC TUBULINS AND USE THEREOF

INTRODUCTION

This patent application is a U.S. National Stage Application of PCT/US2010/031569 filed Apr. 19, 2010 and claims priority to U.S. Patent Application Ser. No. 61/173,687, filed Apr. 29, 2009, the contents of each of which are incorporated herein by reference in their entirety.

This invention was made with government support under grant number F32 AR054653 awarded by the National Institutes of Health. The government has certain rights in the invention.

BACKGROUND OF THE INVENTION

Microtubules, along with actin and intermediate filaments, are the three components of the cellular cytoskeleton. Microtubules are hollow tube-like structures composed of linear protofilaments that are assembled from dimers of α- and β-tubulin. These rigid structures are larger than both actin and intermediate filaments, have an outer diameter of about 25 nm with a luminal diameter of about 18 nm (Howard (2001) *Mechanics of Motor Proteins and the Cytoskeleton* (Sinauer Associates, Inc.)), and can be between 1 μm and 1 mm long (Wade & Chretien (1993) *J. Struct. Biol.* 110:1-27). Microtubules are dynamic filaments, able to polymerize and depolymerize in a regulated manner, and are therefore used in many cellular processes (Desai & Mitchison (1997) *Ann. Rev. Cell Dev. Biol.* 13:83-117; Mitchison & Kirschner (1984) *Nature* 312:237-242). One necessary process is the formation of the mitotic spindle, where microtubules play a critical role in chromosome segregation. In addition, microtubules act as the protein tracks for molecular motor proteins, such as kinesin and dynein.

Tubulin exists as a stable heterodimer containing a non-exchangeable (α-subunit) and exchangeable (β-subunit) guanine nucleotide (GTP) binding site (Amos & Schlieper (2005) *Curr. Opin. Struct. Biol.* 10:236-241). In a growing microtubule, dimers add faster to the plus end. GTP in the β-subunit is slowly hydrolyzed to GDP, but the GTP in the α-subunit is sterically blocked from exchange by the β-subunit, and its GTP is never hydrolyzed (Downing & Nogales (1998) *Curr. Opin. Cell Biol.* 10:16-22; Lowe, et al. (2001) *J. Mol. Biol.* 313:1045-1057; Nogales, et al. (1999) *Cell* 96:79-88; Nogales, et al. (1995) *Nature* 375:424-427). If GTP-bound α/β dimers add to a growing microtubule faster than hydrolysis proceeds, it produces what is known as a GTP cap, which stabilizes the end of the microtubule. Subsequently, if hydrolysis catches up to the microtubule end, the microtubule becomes unstable and depolymerizes in what is called 'catastrophe'. This rather unique behavior of microtubules is referred to as dynamic instability (Desai & Mitchison (1997) *Ann. Rev. Cell Devel. Biol.* 13:83-117; Mitchison & Kirschner (1984) *Nature* 312:237-242), and can be regulated by various microtubule associated proteins, as well as by regulation of tubulin dimer concentrations.

Each tubulin subunit is composed of three domains: an N-terminal nucleotide-binding domain, an intermediate domain, and a C-terminal domain, composed of helices α11/α12 and the acidic C-terminal "tails", which together constitute the binding region for microtubule-based motor proteins (Lowe, et al. (2001) *J. Mol. Biol.* 313:1045-1057; Nogales, et al. (1995) *Nature* 375:424-427). The α/β tubulin heterodimers interact with each other longitudinally (head-to-tail) to form long, rod-like polymers called protofilaments. Between 10 and 15 (but generally 13 in vivo) parallel protofilaments interact laterally (side-by-side) to form a hollow cylindrical structure. The structural polarity of the microtubule gives rise to different rates of polymerization at either end. The rapidly polymerizing end of the microtubule is designated as the plus-end, while the slow growing end is called the minus-end. Different microtubule-based motor proteins have been shown to move along the microtubule track in one direction or the other, as well as regulating the polymerization and depolymerization dynamics.

A number of bacterial homologues of tubulin have been identified and structurally characterized. Among these are FtsZ (Lowe & Amos (1998) *Nature* 391:203-206), BtubA/B (Jenkins, et al. (2002) *Proc. Natl. Acad. Sci. USA* 99:17049-17054; Schlieper, et al. (2005) *Proc. Natl. Acad. Sci. USA* 102:9170-9175; Sontag, et al. (2005) *J. Cell Biol.* 169:233-238), TubZ (Chen & Erickson (2008) *J. Biol. Chem.* 283:8102-8109; Larsen, et al. (2007) *Genes Dev.* 21:1340-1352) and RepX (Pogliano (2008) *Curr. Opin. Cell Biol.* 20:19-27). While FtsZ is a very distant relative of eukaryotic α/β tubulin, BtubA/B are more closely related, and may even have been horizontally transferred into bacteria from eukaryotes (Schlieper, et al. (2005) supra). BtubA/B proteins form dimers in a manner very similar to α/β tubulin, and these dimers can form protofilaments in a GTP-dependent manner (Schlieper, et al. (2005) supra; Sontag, et al. (2005) supra). Although microtubule-like structures have not been observed for BtubA/B, the protofilaments are able to associate, forming twisted pairs as well as bundles. The overall protein fold of BtubA/B is very similar to eukaryotic tubulin (~1.7 Å root mean square displacement between ~360 amino acid α-carbons) despite modest sequence identity (31%-37%). In the crystal structure of the BtubA/B dimer, BtubA (corresponding to β-tubulin) was bound to GDP while the nucleotide binding site of BtubB (corresponding to α-tubulin) was empty.

SUMMARY OF THE INVENTION

The present invention features a hybrid *Prosthecobacter*-eukaryotic tubulin A protein with an amino acid sequence having at least 90% sequence identity with the amino acid sequence of *Prosthecobacter* tubulin A, wherein the surface amino acid residues of *Prosthecobacter* tubulin A have been replaced with the corresponding surface amino acid residues of eukaryotic tubulin β. In one embodiment, the *Prosthecobacter* tubulin A is set forth in SEQ ID NO:7. In another embodiment, the eukaryotic tubulin β is mammalian. In a further embodiment, the surface amino acid residues of *Prosthecobacter* tubulin A are set forth in Table 2. In a particular embodiment, the amino acid substitutions of the hybrid protein are set forth in Table 4. A hybrid protein further including a eukaryotic C-terminus is also embraced by the invention, wherein the eukaryotic C-terminus is selected from the group of SEQ ID NO:12, SEQ ID NO:13, SEQ ID NO:14, and SEQ ID NO:15.

The present invention further features a hybrid *Prosthecobacter*-eukaryotic tubulin B protein with an amino acid sequence having at least 90% sequence identity with the amino acid sequence of *Prosthecobacter* tubulin B, wherein the surface amino acid residues of *Prosthecobacter* tubulin B have been replaced with the corresponding surface amino acid residues of eukaryotic tubulin α. In one embodiment, the *Prosthecobacter* tubulin B comprises SEQ ID NO:8. In another embodiment, the eukaryotic tubulin α is mammalian. In a further embodiment, the surface amino acid residues of *Prosthecobacter* tubulin B are set forth in Table 2. In a particular embodiment, the hybrid tubulin B protein has the amino acid substitutions set forth in Table 4. A hybrid tubulin B protein further including a eukaryotic C-terminus is also embraced by the invention, wherein the eukaryotic C-terminus is selected from the group of SEQ ID NO:9, SEQ ID NO:10, and SEQ ID NO:11.

An isolated hybrid *Prosthecobacter*-eukaryotic tubulin heterodimer is further featured. The heterodimer of the invention is composed of tubulin proteins with amino acid sequences having at least 90% sequence identity with the amino acid sequences of SEQ ID NO:7 and SEQ ID NO:8, wherein the surface amino acid residues of SEQ ID NO:7 and SEQ ID NO:8 have been replaced with the corresponding surface amino acid residues of eukaryotic tubulin β and tubulin α, respectively. In particular embodiments, the hybrid *Prosthecobacter*-eukaryotic tubulin heterodimer has the amino acid substitutions set forth in Table 4. In further embodiments, the hybrid *Prosthecobacter*-eukaryotic tubulin proteins of the heterodimer further include eukaryotic C-termini.

Isolated nucleic acid molecules encoding the hybrid tubulin proteins of the invention as well as host cells containing the same are also provided, as is a method for identifying agents that modulate the activity of the *Prosthecobacter*-eukaryotic tubulin heterodimer.

BRIEF DESCRIPTION OF THE DRAWINGS

FIG. 1 shows an amino acid sequence alignment of wild-type *Prosthecobacter* tubulin A (FIG. 1A) and tubulin B (FIG. 1B) subunits. Pdej, *P. dejongeii*; Pdeb, *P. debontii*; Pvan, *P. vanneervenii*; Cons., Conserved residues.

DETAILED DESCRIPTION OF THE INVENTION

Microtubules are a critical component of the cellular cytoskeleton, serving both structural and functional roles. Although their unique characteristics allow then to dynamically grow and shrink in a GTP and tubulin dependent manner, it is clear that active regulation by proteins plays a critical role during the cell cycle. Additionally, microtubule-based motor proteins use microtubules as tracks upon which to move cargo during active transport. Understanding the structural and mechanistic details of protein-microtubule interactions is therefore of paramount importance. Although great progress has been made in studying these interactions, the heterogeneous nature of naturally derived tubulin presents a major challenge to the field. Conventional tubulin is purified from brain tissue, and has significant drawbacks, including the propensity to polymerize at the concentration of protein necessary for high resolution structural studies thereby precluding formation of the protein crystals necessary for structure determination; and tubulin protein purified from natural sources (most commonly bovine or porcine brain) exists in multiple isoforms that are differentially post-translationally modified, and such heterogeneous proteins cannot be crystallized.

Using a protein engineering approach, the surface of two prokaryotic "tubulin-like" proteins, BtubA and BtubB have now been redesigned to mimic the surface of eukaryotic tubulin by mutating surface amino acid residues to the corresponding amino acids in eukaryotic tubulin. By mutating only surface residues, the hydrophobic core of the heterodimer is not altered thereby allowing folding in the same manner as wild-type heterodimer. This hybrid prokaryotic-eukaryotic tubulin heterodimer provides a homogenous tubulin protein preparation for use in biochemical assays and structural research as well as in screening assays for agents that modulate protofilament formation or interactions with motor proteins. In so far as cell division depends on the proper formation of the microtubule-based mitotic spindle, regulators of microtubule dynamics and proteins involved in spindle formation and action are attractive targets for anticancer drugs. The hybrid prokaryotic-eukaryotic tubulin heterodimer of this invention will enable and simplify the investigation of the role of tubulin and the visualization of protein-tubulin interactions, leading to the development of therapeutics against a broad range of diseases.

According to the present invention, a hybrid prokaryotic-eukaryotic tubulin heterodimer contains prokaryotic tubulin A and B subunits, which have been mutated so that the selected surface amino acid residues of the prokaryotic tubulin A and B subunits have been replaced with the surface residues from eukaryotic tubulin α and β subunits. Hybrid subunits of the invention will possess at least 80% sequence identity, preferably at least 90% sequence identity, more preferably at least 92% sequence identity with native prokaryotic tubulin A and B subunits. Percentage sequence identity is determined, for example, by the Fitch, et al. (1983) *Proc. Nat. Acad. Sci. USA* 80:1382-1386, version of the algorithm described by Needleman, et al. (1970) *J. Mol. Biol.* 48:443-453, after aligning the sequences to provide for maximum homology. Native or wild-type prokaryotic tubulin A and B subunits refer to polypeptides which have not been mutated. In particular embodiments, the prokaryotic tubulin A and B subunits are obtained from a bacterium of the genera *Prosthecobacter*. Native or wild-type *Prosthecobacteri* tubulin A and B subunits, also referred to respectively as bTubA and bTubB, are known in the art and have an amino acid sequence as set forth in Table 1.

TABLE 1

| *Prosthecobacter* sp. | Tubulin | GenBank Accession No. | SEQ ID NO: |
| --- | --- | --- | --- |
| *P. dejongeii* | bTubA | AAO12155 | 1 |
|  | bTubB | AAO12159 | 2 |
| *P. vanneervenii* | bTubA | CAJ14012 | 3 |
|  | bTubB | CAJ14013 | 4 |
| *P. debontii* | bTubA | CAJ14017 | 5 |
|  | bTubB | CAJ14023 | 6 |

In particular embodiments, the native or wild-type *Prosthecobacteri* tubulin A and B subunits have an amino acid sequence as set forth in SEQ ID NO:7 and SEQ ID NO:8, respectively (FIG. 1).

For the purposes of the present invention, surface amino acid residues of tubulin refer to those residues, which upon folding and dimerization, are presented on the exterior of the heterodimer. In this regard, it is the surface residues of the heterodimer that interact with other proteins, e.g., motor proteins. Surface amino acid residues of *Prosthecobacteri* tubulin A and B subunits, which are mutated in accordance the present invention include, but are not limited to, those set forth in Table 2.

TABLE 2

| Tubulin Subunit | Surface Residue* |
| --- | --- |
| bTubA | 157, 160, 162, 164-165, 194-195, 197-199, 268, 348, 409, 411-412, 414-415, 418-419, 421-422, 425-426, 429, 431-432 |

TABLE 2-continued

| Tubulin Subunit | Surface Residue* |
|---|---|
| bTubB | 106-108, 191-192, 195, 260, 262-263, 389-392, 399-401, 404-407, 409-410, 413-414, 417, 419-421, 424-426 |

*Residue of bTubA or bTubB is with reference to SEQ ID NO: 7 or SEQ ID NO: 8, respectively.

A eukaryotic surface residue that corresponds to a prokaryotic surface residue is intended to mean a residue that resides in the same location on both the eukaryotic and prokaryotic proteins. The determination of surface residues can be based upon protein structure analysis derived from three-dimensional crystal structures or predicted secondary and tertiary protein folding. For example, the crystal structure of the bacterial tubulin heterodimer is available under PDB ID: 2BTQ and the bovine tubulin heterodimer under PDB ID: 1TUB. Advantageously, substitution or replacement of surface amino acid residues of prokaryotic tubulin A and tubulin B with corresponding eukaryotic residues allows for the surface of the prokaryotic tubulin to mimic a eukaryotic tubulin heterodimer.

According to the invention, surface residues of eukaryotic tubulin α and tubulin β can be derived from animal, plant, fungi, or insect tubulin protein sequences. In particular embodiments, surface residues of eukaryotic tubulin α and tubulin β are derived from mammalian tubulin protein sequences. By way of illustration, Table 3 lists the surface residues of bTubA and bTubB which were replaced with the surface residues of bovine tubulin α and tubulin β. It should be noted that the structure of BtubA is most similar to β-tubulin, and BtubB is most similar to α-tubulin. Therefore, substitutions in BtubA are from corresponding residues in bovine tubulin β, whereas substitutions in BtubB are from corresponding residues in bovine tubulin α.

TABLE 3

| bTubA Substitutions* | bTubB Substitutions* |
|---|---|
| E157S | Y106H |
| K160R | N107Y |
| K162E | V108T |
| G164P | Q191H |
| E165D | R192T |
| N194H | D195E |
| T195Q | F260Y |
| R197V | G262R |
| R198E | N263G |
| S199N | F389Y |
| S268R | D390A |
| Y348E | N391K |
| S409D | H392R |
| E411M | E399V |
| Q412E | N400G |
| N414T | A401E |
| V415E | S404E |
| A418S | R405E |
| S419N | D406G |
| Q421N | M407E |
| E422D | A409S |
| Q425S | K410E |
| S426E | N413E |
| V429Q | Q414D |
| E431Q | T417A |
| E432D | A419E |
|  | Q420K |
|  | S421D |
|  | D424E |
|  | A425V |
|  | S426G |

*Residues are with reference to P. dejongeii tubulin A and tubulin B.

Based upon the illustrative amino acid substitutions of bacterial tubulin A and B subunits with the surface residues of tubulin α and β from Bos taurus (e.g., Tubα, GENBANK Accession No. NP_001029376; Tubβ, GENBANK Accession No. NP_001003900), similar amino acid residue substitutions are made using the surface residues of other eukaryotic tubulin protein sequences. Mammalian tubulin protein sequences are known in the art and include, but are not limited to, tubulin from *Rattus norvegicus* (e.g., Tubα, GENBANK Accession No. NP_001019510; Tubβ, GENBANK Accession No. NP_001102589); *Mus musculus* (e.g., Tubα, GENBANK Accession No. NP_059075; Tubβ, GENBANK Accession No. NP_033476); *Homo sapiens* (e.g., Tubα, GENBANK Accession No. NP_061816; Tubβ, GENBANK Accession No. NP_006077); and *Sus scrofa* (e.g., Tubα, GENBANK Accession No. NP_001038009; Tubβ, GENBANK Accession No. NP_001107168). Tubulin protein sequences from other eukaryotes are also known in the art and include, but are not limited to, those from plants such as *Zea mays* (e.g., Tubα, GENBANK Accession No. CAD20822; Tubβ, GENBANK Accession No. CAA37060), *Arabidopsis thaliana* (e.g., Tubα, GENBANK Accession No. NP_175423; Tubβ, GENBANK Accession No. AAM10035), or *Oryza sativa* (e.g., Tubα, GENBANK Accession No. AAG16905; Tubβ, GENBANK Accession No. CAA55021); fungi such as *Saccharomyces cerevisiae* (e.g., Tubα, GENBANK Accession No. NP_013625; Tubβ, GENBANK Accession No. BAA09202), *Schizosaccharomyces pombe* (e.g., Tubα, GENBANK Accession No. NP_595106; Tubβ, GENBANK Accession No. NP_596650), or *Neurospora crassa* (e.g., Tubα, GENBANK Accession No. CAA55940; Tubβ, GENBANK Accession No. AAA33617); and insects such as *Drosophila melanogaster* (e.g., Tubα, GENBANK Accession No. NP_476772; Tubβ, GENBANK Accession No. NP_523842) or *Bombyx mori* (e.g., Tubα, GENBANK Accession No. NP_001036884; Tubβ, GENBANK Accession No. NP_001036965). Exemplary amino acid substitutions of surface amino acid residues of SEQ ID NO:7 and SEQ ID NO:8 with corresponding eukaryotic amino acid residues of tubulin β and tubulin α, respectively, are listed in Table 4.

TABLE 4

| bTubA Residue | Eukaryotic β Tubulin Substitution | bTubB Residue | Eukaryotic α Tubulin Substitution |
|---|---|---|---|
| 157 | Ser or gly | 106 | His |
| 160 | Arg | 107 | Tyr |
| 162 | Glu | 108 | Thr |
| 164 | Pro | 191 | His |
| 165 | Asp | 192 | Thr, Ser or Ala |
| 194 | His | 195 | Glu or Asp |
| 195 | Gln | 260 | Tyr or Phe |
| 197 | Val or Leu | 262 | Arg |
| 198 | Glu or Gln | 263 | Gly, Ile or Val |
| 199 | Asn or His | 389 | Tyr |
| 268 | Arg | 390 | Ala or Ser |
| 348 | Glu | 391 | Lys |
| 409 | Asp | 392 | Arg |
| 411 | Met, Ser or Leu | 399 | Val |
| 412 | Glu | 400 | Gly |
| 414 | Thr, Val or Ser | 401 | Glu |
| 415 | Glu | 404 | Glu |
| 418 | Ser | 405 | Glu |
| 419 | Asn or Asp | 406 | Gly |
| 421 | Asn or Arg | 407 | Glu |
| 422 | Asp | 409 | Ser or Thr |
| 425 | Ser | 410 | Glu |
| 426 | Glu | 413 | Glu |
| 429 | Gln | 414 | Asp |

TABLE 4-continued

| bTubA Residue | Eukaryotic β Tubulin Substitution | bTubB Residue | Eukaryotic α Tubulin Substitution |
|---|---|---|---|
| 431 | Gln | 417 | Ala or Ser |
| 432 | Asp | 419 | Glu |
| | | 420 | Lys or Arg |
| | | 421 | Asp |
| | | 424 | Glu |
| | | 425 | Val |
| | | 426 | Gly or Ala |

Accordingly, the present invention embraces substitution or replacement of surface amino acid residues of prokaryotic tubulin A and tubulin B with the corresponding eukaryotic residues set forth in Table 4. In particular embodiments, the present invention embraces tubulin A (SEQ ID NO:7) and B (SEQ ID NO:8) proteins with the amino acid substitutions listed in Table 4. In accordance with this embodiment, the invention embraces hybrid *Prosthecobacter*-eukaryotic tubulin proteins and a heterodimer composed of the same.

The C terminus of tubulin has been shown to be involved in cytoplasmic dynein and kinesin binding and processivity (Wang & Sheetz (2000) *Biophys J.* 78(4):1955-1964; Skiniotis, et al. (2004) *EMBO J.* 23(5):989-999), and binding microtubule-associated protein 2 or tau (Littauer, et al. (1986) *Proc. Natl. Acad. Sci. USA* 83(19):7162-6). Thus, in addition to the above-referenced amino acid substitutions or replacements of surface amino acid residues of prokaryotic tubulin A and tubulin B with corresponding eukaryotic residues, certain embodiments further embrace the addition or fusion of the C-terminal tail of eukaryotic tubulin to the C-terminus of the prokaryotic tubulin proteins. According to this invention, the C-terminus of eukaryotic tubulin α and tubulin β is intended to mean the last (i.e., C-terminal) 50, 40, 30, or 20 amino acid residues of eukaryotic tubulin α and tubulin β proteins. In one embodiment, the C-terminus of eukaryotic tubulin α is intended to include the last 13 to 20, 14 to 18, or 15 to 16 amino acid residues of a eukaryotic tubulin α protein. In another embodiment, the C-terminus of eukaryotic tubulin β is intended to include the last 15 to 25, 16 to 20, or 18 to 19 amino acid residues of a eukaryotic tubulin α protein. Exemplary C-termini of eukaryotic tubulin α include, but are not limited to, VDSVEGEGEEEGEEY (SEQ ID NO:9), ADSAEGDDEGDEY (SEQ ID NO:10), and VGTDSFEEE-NEGEEF (SEQ ID NO:11). Exemplary C-termini of eukaryotic tubulin β include, but are not limited to, ATADEQGE-FEEEGEEDEA (SEQ ID NO:12), ATADEQGEFEEEEGEDEA (SEQ ID NO:13), ATAEEE-GEFEEEAEEEVA (SEQ ID NO:14), and ATAEEEGE-FEEEAEDDA (SEQ ID NO:15). Additional eukaryotic tubulin C-termini are known and readily obtained from sequences available from sources such as GENBANK and EMBL databases. Preferably, the C-terminal 18 amino acid residues of eukaryotic tubulin β are added to the C-terminus of bTubA and the C-terminal 15 amino acid residues of eukaryotic tubulin α are added to the C-terminus of bTubB.

There are a variety of ways in which one can make the hybrid tubulin proteins of the invention. In one embodiment of this invention, a hybrid tubulin protein is prepared by introducing multiple amino acid substitutions simultaneously or consecutively introducing single amino acid substitutions into a prokaryotic tubulin protein. For convenience, substitutions in the amino acid sequence of native prokaryotic tubulin protein are usually made by introducing mutations into the corresponding nucleotide sequence of the DNA encoding native prokaryotic tubulin protein, for example by site-directed mutagenesis. Expression of the mutated DNA then results in production of the hybrid tubulin protein having the desired (non-native) amino acid sequence. Whereas any technique known in the art can be used to perform site-directed mutagenesis, e.g., as disclosed in Sambrook, et al. ((1989) *Molecular Cloning: A Laboratory Manual*, Second Edition, Cold Spring Harbor Laboratory Press, New York), oligonucleotide-directed mutagenesis is a preferred method for preparing the hybrid tubulin proteins of this invention. This method, which is well-known in the art (Zoller, et al. (1983) *Meth. Enzymol.* 100:4668-500; Zoller, et al. (1987) *Meth. Enzymol.* 154:329-350; Carter (1987) *Meth. Enzymol.* 154: 382-403; Kunkel, et al. (1987) *Meth. Enzymol.* 154:367-382; Horwitz, et al. (1990) *Meth. Enzymol.* 185:599-611), is particularly suitable for making hybrid tubulin proteins.

The site-directed mutagenesis technique typically employs a phage vector that exists in both a single-stranded and double-stranded form. Typical vectors useful in site-directed mutagenesis include vectors such as the M13 phage, and plasmid vectors that contain a single-stranded phage origin of replication (Messing, et al. (1983) *Meth. Enzymol.* 101:20-78; Veira, et al. (1987) *Meth. Enzymol.* 153:3-11; Short, et al. (1988) *Nuc. Acids. Res.* 16:7583-7600). Replication of these vectors in suitable host cells results in the synthesis of single-stranded DNA that may be used for site-directed mutagenesis.

Of course, site-directed mutagenesis may be used to introduce multiple substitutions into a starting DNA. If the sites to be mutated are located close together, the mutations can be introduced simultaneously using a single oligonucleotide that encodes all of the desired mutations. If, however, the sites to be mutated are located some distance from each other (separated by more than about ten nucleotides), it is more difficult to generate a single oligonucleotide that encodes all of the desired changes. Instead, one of two alternative methods may be employed.

In one method, a separate oligonucleotide is generated for each desired mutation. The oligonucleotides are then annealed to the single-stranded template DNA simultaneously, and the second strand of DNA that is synthesized from the template will encode all of the desired amino acid substitutions.

In an alternative method, two or more rounds of mutagenesis are used to produce the desired variant. The first round is as described for introducing a single mutation. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis (Higuchi (1990) *PCR Protocols*, pp. 177-183, Academic Press; Vallette, et al. (1989) *Nucl. Acids Res.* 17:723-733) is also suitable for making the hybrid tubulins of the invention. Briefly, when small amounts of template DNA are used as starting material in a PCR, primers that differ slightly in sequence from the corresponding region in the template DNA can be used to generate relatively large quantities of a specific DNA fragment that differs from the template sequence only at the positions where the primers differ from the template. For introduction of a mutation into a plasmid DNA, for example, the sequence of one of the primers includes the desired mutation and is designed to hybridize to one strand of the plasmid DNA at the position of the mutation; the sequence of the other primer must be identical to a nucleotide sequence within the opposite strand of the plasmid DNA, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone. See also, Wagner, et al. (1991) *PCR Topics*, pp. 69-71, Springer-Verlag.

Another method for preparing hybrid tubulin proteins is cassette mutagenesis, which is based on the technique described by Wells, et al. (1985) *Gene* 34:315-323. The starting material is the plasmid (or other vector) carrying the DNA sequence to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. The resulting plasmid contains the mutated DNA sequence.

The presence of mutation(s) in a DNA is determined by methods well-known in the art, including restriction mapping and/or DNA sequence analysis, e.g., by the dideoxy chain termination method of Sanger, et al. (1979) *Proc. Nat. Acad. Sci. USA* 72:3918-3921.

DNA encoding a hybrid tubulin of the invention is inserted into a replicable vector for further cloning or expression. "Vectors" are plasmids and other DNAs that are capable of replicating within a host cell, and as such, are useful for performing two functions in conjunction with compatible host cells (a vector-host system). One function is to facilitate the cloning of the nucleic acid that encodes a hybrid tubulin, i.e., to produce usable quantities of the nucleic acid. The other function is to direct the expression of a hybrid tubulin. One or both of these functions are performed by the vector in the particular host cell used for cloning or expression. The vectors will contain different components depending upon the function they are to perform.

To produce a hybrid tubulin, an expression vector will include DNA encoding the hybrid tubulin, as described above, operably linked to a promoter and a ribosome binding site. The hybrid tubulin then is expressed directly in recombinant cell culture, or as a fusion with a heterologous polypeptide, preferably a signal sequence or other polypeptide having a specific cleavage site at the junction between the heterologous polypeptide and the hybrid tubulin.

"Operably linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

In some embodiments the hybrid tubulin A protein and hybrid tubulin B protein of the invention are expressed individually in separate host cells. In other embodiments, the hybrid tubulin proteins of the invention are coexpressed in the same host cell, e.g., from the same expression vector.

Prokaryotes (e.g., *E. coli*, and other bacteria) are the preferred host cells for the initial cloning steps of this invention. They are particularly useful for rapid production of large amounts of DNA, for production of single-stranded DNA templates used for site-directed mutagenesis, and for DNA sequencing of the hybrids generated. Prokaryotic host cells also can be used for expression of DNA encoding hybrid tubulin proteins. Polypeptides that are produced in prokaryotic cells typically will be non-glycosylated.

In addition, the hybrid tubulin proteins of this invention can be expressed in eukaryotic host cells, including eukaryotic microbes (e.g., yeast), plant cells, or cells derived from an animal or other multicellular organism (e.g., Chinese hamster ovary cells, and other mammalian cells), or in live animals (e.g., cows, goats, sheep).

Cloning and expression methodologies are well-known in the art. Examples of prokaryotic and eukaryotic host cells, and expression vectors, suitable for use in producing the hybrid tubulin proteins of the present invention are, for example, those disclosed in WO 90/07572.

If prokaryotic cells or cells that contain substantial cell wall constructions are used as hosts, the preferred methods of transfection of the cells with DNA is the calcium treatment method described by Cohen et al. ((1972) *Proc. Natl. Acad. Sci.* 69:2110-2114) or the polyethylene glycol method of Chung et al. ((1988) *Nuc. Acids. Res.* 16:3580). If yeast are used as the host, transfection is generally accomplished using polyethylene glycol, as taught by Hinnen ((1978) *Proc. Natl. Acad. Sci. USA* 75:1929-1933). If mammalian cells are used as host cells, transfection generally is carried out by the calcium phosphate precipitation method of Graham, et al. ((1978) *Virology* 52:546) or Gorman, et al. ((1990) *DNA and Protein Eng. Tech.* 2:3-10). However, other known methods for introducing DNA into prokaryotic and eukaryotic cells, such as nuclear injection, electroporation, particle bombardment, *Agrobacterium*-mediated transformation, or protoplast fusion also are suitable for use in this invention.

Hybrid tubulin proteins preferably are secreted from the host cell in which it they are expressed, in which case the proteins are recovered from the culture medium in which the host cells are grown. In that case, it may be desirable to grow the cells in a serum free culture medium, since the absence of serum proteins and other serum components in the medium may facilitate purification of the hybrid tubulin proteins. If it is not secreted, then the hybrid tubulin proteins are recovered from lysates of the host cells. When the hybrid tubulin proteins are expressed in a host cell other than one of human origin, the hybrid tubulin proteins will be completely free of proteins of human origin. In any event, it will be necessary to purify the hybrid tubulin proteins from recombinant cell proteins in order to obtain substantially homogeneous preparations of the hybrid tubulin proteins.

Generally, purification of a hybrid tubulin protein is accomplished by taking advantage of the differential physicochemical properties of the hybrid tubulin protein as compared to the contaminants with which it may be associated. For example, as a first step, the culture medium or host cell lysate is centrifuged to remove particulate cell debris. The hybrid tubulin protein thereafter is purified from contaminant soluble proteins and polypeptides, for example, by ammonium sulfate or ethanol precipitation, gel filtration (molecular exclusion chromatography), ion-exchange chromatography, hydrophobic chromatography, immunoaffinity chromatography (e.g., using a column containing anti-tubulin antibodies coupled to SEPHAROSE), cation exchange chromatography (WO 93/25670), reverse phase HPLC, and/or gel electrophoresis.

In a further embodiment of this invention, a hybrid tubulin protein will include one or more additional amino acid sequence mutations, tags, or other modifications, e.g., modifications that facilitate or block the assembly of the hybrid proteins into protofilament microtubules or facilitate or block interactions with associated proteins.

Antibodies to hybrid tubulin proteins of the invention are also contemplated. Such antibodies are produced by immunizing an animal with a hybrid tubulin protein or a fragment thereof, optionally in conjunction with an immunogenic polypeptide, and thereafter recovering antibodies from the serum of the immunized animals. Alternatively, monoclonal antibodies are prepared from cells of the immunized animal in conventional fashion. The antibodies also can be made in the form of chimeric (e.g., humanized) or single chain antibodies or Fab fragments, using methods well-known in the art. Preferably, the antibodies will bind to the hybrid tubulin protein but will not substantially bind to (i.e., cross react with) other native tubulin proteins (such as native human, bovine, or prokaryotic tubulin). The antibodies can be used in methods relating to the localization and assembly of the hybrid tubulin proteins. Immobilized antibodies are particularly useful in the purification of the hybrid tubulin proteins, for example from recombinant cell cultures.

The hybrid tubulin proteins of the invention find application in studying tubulin dimerization, protofilament formation, and motor protein interactions as well as in identifying agents that modulate the activity of tubulin.

It is contemplated that the hybrid tubulins of the invention can be used to generate a crystal structure of tubulin alone or in combination with associated proteins (e.g., kinesin, dynein or other microtubule associated proteins (MAPs)). Once the three-dimensional structure of the hybrid tubulin is determined, a potential modulatory agent can be examined through the use of computer modeling using a docking program such as GRAM, DOCK, or AUTODOCK (Dunbrack, et al. (1997) *Folding & Design* 2:27-42). This procedure can include computer fitting of potential agents to the tubulin dimer to ascertain how well the shape and the chemical structure of the potential ligand will interact with the tubulin dimer. Computer programs can also be employed to estimate the attraction, repulsion, and steric hindrance of the test agent. Generally the tighter the fit (e.g., the lower the steric hindrance, and/or the greater the attractive force) the better substrate the agent will be since these properties are consistent with a tighter binding constraint. Furthermore, the more specificity in the design of a potential test agent the more likely that the agent will not interfere with related mammalian proteins. This will minimize potential side-effects due to unwanted interactions with other proteins.

In addition to in silico screening, the invention also embraces in vitro and in vivo screening of test agents which involves contacting the hybrid *Prosthecobacter*-eukaryotic tubulin heterodimer of the invention with a test agent and determining whether the test agent modulates the activity of the *Prosthecobacter*-eukaryotic tubulin heterodimer as compared to a control, e.g., a heterodimer not contacted with the test agent. Tubulin activities which can be monitored include, but are not limited to, dimerization, GTPase activity, polymerization into protofilaments, and/or interaction with associated proteins. Test agents which can be screened in accordance with the present invention can be from any source and can be any type of molecule, e.g., protein, carbohydrate, nucleic acid, small organic compound, natural product, antibody, and the like. Agents identified by the method of the invention find application in the treatment of diseases or conditions such as cancer.

The invention is described in greater detail by the following non-limiting examples.

Example 1

Hybrid Bacterial-Bovine Tubulins

Using a model of the kinesin motor domain-microtubule complex derived from cryo-EM reconstruction (Kifla-AMP-PNP, Protein Data Base ID 2HXF) (Kikkawa & Hirokawa (2006) *EMBO J.* 25:4187-4194), BtubA and BtubB (PDB, 2BTQ) were aligned with α and β tubulin. It should be noted that BtubA is most homologous to (β-tubulin, and BtubB is most homologous with α-tubulin. Residues in BtubA/B residues within 8 Å of the docked kinesin motor domain were identified. In so far as it was desired to avoid any mutations that would result in misfolding, or even decrease the folding efficiency of the hybrid genes, all of these residues were individually checked to ensure that they were significantly solvent exposed and that they did not participate in any interactions with the core amino acids. Following this analysis, 57 amino acids were identified for mutagenesis, 26 in BtubA in order to make its surface like β-tubulin, and 31 in BtubB to make it resemble α-tubulin. A structural alignment of BtubA with β-tubulin using the protein structure comparison service SSM at European Bioinformatics Institute (Krissinel & Henrick, 2004) *Acta Crystallogr. D Biol. Crystallogr.* 60:2256-2268), produced a root mean square deviation (RMSD) of 1.75 Å over 397 amino acid α-carbons. A similar alignment of BtubB with α-tubulin resulted in an RMSD of 1.66 Å over 360 amino acid α-carbons. Due to this close alignment, it was contemplated that the overall core of the proteins were very similar, and therefore surface mutations would produce an interface closely resembling eukaryotic tubulin. Following design, these hybrid tubulins were modeled in order to assess whether the shape and surface charge characteristics would resemble bovine tubulin. This analysis indicated that the electrostatic surface of the hybrid tubulin very closely resembled that of bovine tubulin. Note that the bacterial tubulin template, contoured in the same manner, looks very different. No energy minimization was performed, so the specific position of side chains was approximate, but the overall charge characteristics were expected to be quite accurate.

These hybrid genes, (named HtubA and HtubB for "Hybrid tubulin A and B") were then cloned into *E. coli* pET-based expression vectors and the overexpressed proteins were purified using a combination of standard protein purification strategies including ion exchange and Ni-NTA affinity chromatography. Both HtubA and HtubB constructs contained a polyhistidine purification tag, and the HtubA protein also contained an N-terminal thioredoxin tag. Yields of purified protein were 10 mg HtubA per 1 L starting culture and 5 mg HtubB per 1 L starting culture. Analyses of the activity of HtubA/B indicated the following.

When purified HtubA and HtubB proteins were mixed in a 1:1 stoichiometric ratio and subjected to gel filtration chromatography, they eluted from the column at an apparent molecular weight of a dimer. These results indicate that mixture of HtubA/B protein is associating, while not polymerizing.

When the Eg5 (a kinesin-5) motor domain was mixed in a 1:1 stoichiometric ratio with HtubA/B, and subjected to gel filtration chromatography in the absence of additional salt and ATP, the kinesin-HtubA/B complex eluted from the column at an apparent molecular weight of a trimeric complex. These results indicate that a kinesin motor can bind the HtubA/B dimer.

After adding additional salt and ATP to the Eg5-HtubA/B complex, the proteins were resolved over a gel filtration column, and the kinesin was found to have dissociated from the HtubA/B complex. These results are consistent with how a kinesin interacts with eukaryotic microtubules.

The Eg5-HtubA/B complex was rapidly mixed with fluorescent MANT-ATP in a stopped-flow instrument. This experiment was designed to monitor the kinetics of ATP binding to kinesin in the absence and presence of HtubA/B. In the absence of HtubA/B, the rate of ATP binding was 0.5-1 sec−1 and in the presence of eukaryotic microtubules, the rate of ATP binding was 25-30 sec−1. When the kinesin-HtubA/B complex was mixed with MANT-ATP, a rate of ATP binding of 265±14 sec−1 was observed. These results indicate that the HtubA/B complex stimulates the rate of ATP binding to kinesin.

Taken together, these results indicate that hybrid bacterial-eukaryotic tubulin protein can be expressed and purified, fold properly in bacterial expression systems, and bind to a kinesin motor domain in a manner similar to that observed for eukaryotic microtubules.

Example 2

Characterization of Hybrid Bacterial-Bovine Tubulins

Circular dichroism (CD) spectroscopy is used to demonstrate that HtubA/B resembles bovine tubulin. As the a and β isoforms of bovine tubulin are not stable when separated, HtubA and HtubB are compared alone and in complex with dimeric bovine tubulin under non-polymerizing conditions. Analytical gel filtration and analytical ultracentrifugation are also used to measure complex formation between HtubA and HtubB.

The GTPase activity of HtubA, HtubB, and HtubA/B is determined by measuring the concentration of evolved phosphate, using an improved sensitivity malachite green assay (Geladopoulos, et al. (1991) *Analytical Biochemistry* 192: 112-116) as well as coumarin-labeled phosphate binding protein (MDCC-PBP) coupled assay (Brune, et al. (1994) *Biochemistry* 33:8262-8271) in a stopped-flow instrument. For the MDCC-PBP assay, purified HtubA, HtubB, or HtubA/B are incubated with GTP for increasing time domains, then quenched with acid, followed by neutralization with base. In order to quantify the background level of Pi in the reaction, a zero time point is performed by mixing Htub with acid, followed by addition of GTP and base. Pi is quantified by rapidly mixing the reaction contents at each time point with MDCC-PBP in a stopped-flow instrument (Cochran, et al. (2009) *Cell* 136:110-122).

Polymer formation of HtubA/B is analyzed by pelleting assays. The HtubA construct contains an N-terminal thioredoxin tag in order to assist in expression and block polymerization. Although preliminary data indicate this is not interfering with intra-dimer formation, polymer formation will require HtubA without the thioredoxin tag. This construct is in the background of a pET32b plasmid (Novagen). As such, a thrombin cleavage site follows the thioredoxin tag and polyhistidine purification tag, thereby facilitating the removal of the tag. In order to assay protofilament formation, GTP is added to stimulate polymerization of various molar ratios of HtubA and HtubB, and the reactions are centrifuged in a TLA100 rotor (Beckman Coulter) for 20 minutes at 250,000 g at 20° C. Samples of the supernatant and pellet fractions are resolved by SDS-PAGE. HtubA/B polymer formation can also be analyzed by static 90° light scattering experiments using a fluorimeter with excitation and emission wavelengths set to 350 nm and a slit width of 3 nm. GTP is added to initiate polymerization and the critical concentration for protofilament bundle formation is determined.

Negative stained electron microscopy is then used to image formation of the HtubA/B protofilament twisted pairs and bundles. Time course EM experiments are performed to determine the early stages of HtubA/B filament formation at low HtubA/B concentrations.

HtubA and HtubB proteins are used individually, and as a dimer, in X-ray diffraction studies to determine their high resolution structure. The conditions for crystallization for BtubA/B (Schlieper, et al. (2005) *Proc. Natl. Acad. Sci. USA* 102:9170-9175) are initially used to design a matrix for crystal screening. Standard hanging drop vapor diffusion methods are used and a number of different screening kits are employed, including the standard sparse matrix sampling conditions as well as polyethylene glycol (PEG) screens. The structures are solved using molecular replacement using existing BtubA/B structures as search models. The high resolution structural analysis of the HtubA/B system alone provides a foundation for addressing any conformational changes in tubulin upon kinesin binding as well as assisting in further surface re-design to achieve a more eukaryotic-like tubulin that can be produced in bacteria.

Example 3

Detailed Structural Characterization of HtubA/B-Motor and HtubA/B-MAP Interactions Atomic resolution crystal structures of a kinesin motor in complex with tubulin as well as microtubule binding domain of cytoplasmic dynein in complex with HtubA/B are determined. Further studies can also utilize the HtubA/B proteins to investigate the structures of other MAPs in complex with HtubA/B.

Analytical gel filtration and analytical ultracentrifugation are used to measure complex formation between HtubA.HtubB as well as between the ternary complex HtubA.HtubB.kinesin. As different kinesin motors have different behaviors and binding affinities to tubulin, several different kinesin motor domain constructs are used for this analysis. Such constructs include, e.g., conventional kinesin (kinesin-1), Eg5 (kinesin-5), Kif18a (kinesin-8), NOD (kinesin-10), MCAK (kinesin-13), Ncd (kinesin-14), and Costal2 (an unclassified kinesin). Each of these motor domains are incubated with preformed HtubA/B and then analyzed using the techniques described above for stability.

Using the MDCC-PBP coupled assay described herein, ATPase stimulation is measured when each of the motor domains incubated with the HtubA/B complex. This is then compared to the ATPase stimulation of the motors in the presence of bovine dimeric tubulin. Other presteady-state kinetic parameters of kinesin in complex with HtubA/B are also measured including rates of ATP and ADP binding and the release rates of ADP and Pi. As described herein, removal of the N-terminal thioredoxin tag should result in the HtubA/B dimer forming polymeric protofilaments similar to those observed for native BtubA/B. Therefore, the filament stimulated ATPase of the various motors is characterize and compared to that of the dimer stimulated motor ATPase.

During the process of the characterization studies described herein, it will become clear which motors bind to HtubA/B, and which conditions favor formation and stabilization of this complex. In this regard, it may be necessary to use the thioredoxin tagged HtubA to inhibit polymerization. Alternately, mutants in the dimer-dimer interface can be engineered that would block polymerization.

Given that structures of many of the kinesin motor domains are available, and that the crystal structure of BtubA/B is also available, solving the structure will likely be possible using molecular replacement phasing. Alternatively, the proteins can be expressed and purified using selenomethionine for MAD, SAD, or SIRAS phasing.

The previously crystallized dynein microtubule binding domain (MTBD) was expressed as a fusion with seryl-tRNA synthetase (SRS) containing 3 heptads in the antiparallel stalk region (Carter, et al. (2008) *Science* (New York, N.Y.) 322: 1691-1695). The microtubule binding domain was 167 amino acids and was a stable, folded extension from the SRS fusion partner. The microtubule binding domain can be PCR amplified from mouse dynein cDNA and the truncated construct can be cloned into *E. coli* pET-based vectors for overexpression and purification. The purified microtubule binding domain protein is analyzed by CD spectroscopy and analytical ultracentrifugation to ensure proper structure, and is functionally characterized by microtubule co-sedimentation experiments. The microtubule binding domain is then mixed with HtubA/B to obtain crystals and the structure of the MTBD-HtubA/B complex at high resolution is determined.

With the HtubA/B dimer readily available, it is now straightforward to investigate its association with other microtubule associated proteins. As indicated, many of these proteins interact with microtubules though multiple binding sites. As such, microtubule binding domain constructs can be cloned, expressed, and purified for these experiments. Initial targets would be the microtubule binding motifs of tau, MAP2, MAP4, the DCX domain of doublecortin and the human spastin protein, including its AAA domain and its microtubule binding domain. In addition, the interaction of +TIP-HtubA/B complexes will also be determined.

Example 4

Design and Characterization of a Mini-Protofilament

The HtubA/B dimer can be further engineered to form a mini-protofilament composed of an end-to-end dimer of HtubA/B dimers. Such a tetramer will allow for the investigation of motor protein and MAP interactions that involve two binding sites at the intradimer interface, and will also allow for the identification and characterization of interactions at the interdimer interface.

The HtubA/B dimer exemplified herein is blocked from polymerizing at the minus end by the presence of an N-terminal thioredoxin tag on HtubA (HtubA/B-TRX) and removal of this tag by protease cleavage or by expressing the HtubA without the tag results in HtubA/B dimer that can polymerize into protofilaments. In contrast, blocking polymerization at the plus end is more complicated as neither the N- nor C-terminus of HtubB is located in a position such that a tag would block further addition of dimer at the plus end. Therefore, site-directed mutagenesis is used at the plus-end binding interface of HtubB in order to block polymerization. This mutant HtubB would still be able to form normal interactions with HtubA at the minus-end interface, allowing formation of an HtubA/B dimer that is unable to polymerize (hereafter referred to as HtubA/B+). A similar approach has resulted in non-polymerizing mutant actin produced in a Sf9 baculovirus expression system (Joel, et al. (2004) *Biochemistry* 43:11554-11559).

This HtubA/B+ dimer is then mixed with the HtubA/B-TRX dimer. As these two dimer constructs have a mutually compatible interface, they will form a tetramer containing two intradimer interfaces and one interdimer interface (HtubA/B/A/B). If the thioredoxin tag is shown to interfere with complex formation, a similar mutagenic approach could be taken in order to make an HtubA/B dimer blocked from polymerizing at the minus end.

The mechanistic characterizations described herein for the initial HtubA/B-TRX dimer alone and in complex with kinesin motors and MAPs is repeated with the mini-protofilament. Given that kinesins can bind to adjacent tubulin dimers, the HtubA/B/A/B tetramer will be able to form a complex with dimeric kinesins. This is characterized by gel filtration analysis as described herein for dimeric constructs of kinesin-1 and kinesin-5. Complex formation allows for high resolution structural studies to be carried out. A similar approach can be taken in order to characterize constructs of MAPs, such as tau, with two microtubule binding domains.

The surface engineering of the HtubA/B binding interface involved only residues located within 8 Å of the docked kinesin motor domain. While these include virtually the entire surface at the intradimer interface, residues at the interdimer interface formed in the HtubA/B/A/B tetramer will still contain surface residues from the original BtubA/B proteins. This should neither affect formation of the tetramer nor the dimer binding experiments described herein, but it would present a non-eukaryotic surface at this interface. Therefore, the remainder of the surface exposed residues in the region can be mutated to resemble eukaryotic tubulin, thereby producing an HtubA/B/A/B tetramer with a completely eukaryotic surface. To form a protofilament with this complete interface, additional surface mutations can be introduced into the untagged HtubA protein.

With HtubA/B dimer, HtubA/B/A/B tetramer, and HtubA/B protofilaments available, binding of motor proteins as well as other MAPs can be compared. For example, it will be possible to measure differential binding of the complete or fractionated MAP pool that is obtained during a prep of bovine tubulin. During this procedure, a large number of MAPs are separated from purified tubulin and discarded. This pool of MAPs can be assayed to identify differences in binding to HtubA/B dimers, tetramers, and protofilaments. While this will identify a number of known proteins and MAPs, comparison with each other and with bovine microtubules will highlight differences in binding modes, as well as distinguishing between MAPs that bind to the inside/outside of microtubules, or in between adjacent protofilaments. Proteins that bind in specific or unusual ways can then be identified by mass spectrometry analysis.

What is claimed is:

1. An isolated hybrid *Prosthecobacter*-eukaryotic tubulin A protein comprising an amino acid sequence of SEQ ID NO:7, wherein surface amino acid residues of *Prosthecobacter* tubulin A have been replaced with surface amino acid residues of eukaryotic tubulin β as set forth in Table 4.

2. The hybrid protein of claim 1, further comprising a eukaryotic C-terminus.

3. The hybrid protein of claim 2, wherein the eukaryotic C-terminus is selected from the group of SEQ ID NO:12, SEQ ID NO:13, SEQ ID NO:14, and SEQ ID NO:15.

4. The hybrid protein of claim 1, further comprising a hybrid *Prosthecobacter*-eukaryotic tubulin B protein of SEQ ID NO:8, wherein surface amino acid residues of *Prosthecobacter* tubulin B have been replaced with surface amino acid residues of eukaryotic tubulin α as set forth in Table 4.

5. The hybrid protein of claim 4, wherein the hybrid *Prosthecobacter*-eukaryotic tubulin B protein further comprises a eukaryotic C-terminus.

6. The hybrid *Prosthecobacter*-eukaryotic tubulin B protein of claim 5, wherein the eukaryotic C-terminus is selected from the group of SEQ ID NO:9, SEQ ID NO:10, and SEQ ID NO:11.

7. An isolated hybrid *Prosthecobacter*-eukaryotic tubulin heterodimer comprising amino acid sequences of SEQ ID NO:7 and SEQ ID NO:8, wherein surface amino acid residues of SEQ ID NO:7 and SEQ ID NO:8 have been replaced with surface amino acid residues of eukaryotic tubulin β and tubulin α, respectively, as set forth in Table 4.

8. The hybrid *Prosthecobacter*-eukaryotic tubulin heterodimer of claim 7, further comprising eukaryotic C-termini.

9. An isolated nucleic acid molecule encoding the hybrid *Prosthecobacter*-eukaryotic tubulin A protein of claim 1.

10. An isolated nucleic acid molecule encoding the hybrid *Prosthecobacter*-eukaryotic tubulin B protein of claim 4.

11. An isolated host cell comprising the isolated nucleic acid molecule of claim 9.

12. The isolated host cell of claim 11, further comprising an isolated nucleic acid molecule encoding a hybrid *Prosthecobacter*-eukaryotic tubulin B protein with an amino acid sequence of SEQ ID NO:8, wherein surface amino acid residues of SEQ ID NO:8 have been replaced with surface amino acid residues of eukaryotic tubulin α as set forth in Table 4.

13. The isolated host cell of claim 11, wherein said host cell is selected from the group of bacteria, yeast, filamentous fungi, and plant cells.

14. A method for identifying an agent that modulates the activity of tubulin comprising contacting the hybrid *Prosthecobacter*-eukaryotic tubulin heterodimer of claim 7 with a test agent and determining whether the test agent modulates the activity of the *Prosthecobacter*-eukaryotic tubulin heterodimer as compared to a control, thereby identifying an agent that modulates the activity of tubulin.

* * * * *